United States Patent
Rebar

(10) Patent No.: US 10,293,000 B2
(45) Date of Patent: *May 21, 2019

(54) METHODS AND COMPOSITIONS FOR THE TREATMENT OF LYSOSOMAL STORAGE DISEASES

(71) Applicant: Sangamo Therapeutics, Inc., Richmond, CA (US)

(72) Inventor: Edward J. Rebar, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/840,904

(22) Filed: Dec. 13, 2017

(65) Prior Publication Data

US 2018/0110808 A1  Apr. 26, 2018

Related U.S. Application Data

(63) Continuation of application No. 13/839,336, filed on Mar. 15, 2013, now Pat. No. 9,877,988.

(60) Provisional application No. 61/704,072, filed on Sep. 21, 2012, provisional application No. 61/670,463, filed on Jul. 11, 2012.

(51) Int. Cl.
| | | |
|---|---|---|
| A01N 63/00 | (2006.01) | |
| A61K 35/28 | (2015.01) | |
| A61K 38/46 | (2006.01) | |
| A61K 48/00 | (2006.01) | |
| C12N 9/22 | (2006.01) | |
| C12N 15/90 | (2006.01) | |

(52) U.S. Cl.
CPC ............ *A61K 35/28* (2013.01); *A61K 38/46* (2013.01); *A61K 38/465* (2013.01); *A61K 48/005* (2013.01); *C12N 9/22* (2013.01); *C12N 15/907* (2013.01); *A61K 48/00* (2013.01); *C07K 2319/81* (2013.01)

(58) Field of Classification Search
USPC .......................................... 435/325; 424/93.2
See application file for complete search history.

(56) References Cited

U.S. PATENT DOCUMENTS

| | | | |
|---|---|---|---|
| 5,356,802 A | 10/1994 | Chandrasegaran | |
| 5,436,150 A | 7/1995 | Chandrasegaran | |
| 5,487,994 A | 1/1996 | Chandrasegaran | |
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas, III et al. | |
| 6,200,759 B1 | 3/2001 | Dove et al. | |
| 6,242,568 B1 | 6/2001 | Barbas, III et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,534,261 B1 | 3/2003 | Cox, III et al. | |
| 6,599,692 B1 | 7/2003 | Case et al. | |
| 6,607,882 B1 | 8/2003 | Cox, III et al. | |
| 6,689,558 B2 | 2/2004 | Case | |
| 6,723,551 B2 | 4/2004 | Kotin et al. | |
| 6,794,136 B1 | 9/2004 | Eisenberg et al. | |
| 6,824,978 B1 | 11/2004 | Cox, III et al. | |
| 6,903,185 B2 | 6/2005 | Kim et al. | |
| 6,933,113 B2 | 8/2005 | Case et al. | |
| 6,979,539 B2 | 12/2005 | Cox, III et al. | |
| 7,013,219 B2 | 3/2006 | Case et al. | |
| 7,030,215 B2 | 4/2006 | Liu et al. | |
| 7,067,317 B2 | 6/2006 | Rebar et al. | |
| 7,070,934 B2 | 7/2006 | Cox, III et al. | |
| 7,153,949 B2 | 12/2006 | Kim et al. | |
| 7,163,824 B2 | 1/2007 | Cox, III et al. | |
| 7,253,273 B2 | 8/2007 | Collingwood | |
| 7,262,054 B2 | 8/2007 | Jamieson et al. | |
| 7,361,635 B2 | 4/2008 | Miller et al. | |
| 7,888,121 B2 | 2/2011 | Urnov et al. | |
| 8,697,359 B1 | 4/2014 | Zhang | |
| 8,771,945 B1 | 7/2014 | Zhang | |
| 8,771,985 B2 | 7/2014 | Cui et al. | |
| 8,795,965 B2 | 8/2014 | Zhang | |
| 8,865,406 B2 | 10/2014 | Zhang et al. | |
| 8,871,445 B2 | 10/2014 | Cong et al. | |
| 8,889,356 B2 | 11/2014 | Zhang | |
| 8,889,418 B2 | 11/2014 | Zhang et al. | |
| 8,895,308 B1 | 11/2014 | Zhang et al. | |
| 8,906,616 B2 | 12/2014 | Zhang et al. | |
| 8,932,814 B2 | 1/2015 | Cong et al. | |
| 8,945,839 B2 | 2/2015 | Zhang | |
| 8,993,233 B2 | 3/2015 | Zhang et al. | |
| 8,999,641 B2 | 4/2015 | Zhang et al. | |

(Continued)

FOREIGN PATENT DOCUMENTS

| | | |
|---|---|---|
| GB | 2338237 | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |

(Continued)

OTHER PUBLICATIONS

Lysosomal storage diseases, Wikipedia, 2014.*
Li (Nature, Jul. 14, 2011, vol. 475, No. 7355, p. 217-221.*
Anguela, et al., "In Vivo Genome Editing of Liver Albumin for Therapuetic Gene Expression: Rescue of Hemophilic Mice via Integration of Factor 9," 54th Annual Meeting and Exposition, 751 Atlanta, USA (Dec. 10, 2012). abstract. Retrieved from the internet: URL:https://ash.confex.com/ash/2012/webprogram/Paper51404.html.

(Continued)

*Primary Examiner* — Michael C Wilson
(74) *Attorney, Agent, or Firm* — Pasternak Patent Law; Susan Abrahamson

(57) ABSTRACT

Nucleases and methods of using these nucleases for inserting a sequence encoding a therapeutic protein such as an enzyme into a cell, thereby providing proteins or cell therapeutics for treatment and/or prevention of a lysosomal storage disease.

7 Claims, 9 Drawing Sheets
Specification includes a Sequence Listing.

(56) References Cited

U.S. PATENT DOCUMENTS

| | | |
|---|---|---|
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2005/0267061 A1 | 12/2005 | Martin |
| 2006/0063231 A1 | 3/2006 | Li et al. |
| 2006/0153826 A1 | 7/2006 | Arnould et al. |
| 2006/0188987 A1 | 8/2006 | Guschin et al. |
| 2007/0218528 A1 | 9/2007 | Miller |
| 2008/0131962 A1 | 6/2008 | Miller |
| 2008/0159996 A1 | 7/2008 | Ando et al. |
| 2008/0299580 A1 | 12/2008 | DeKelver et al. |
| 2009/0068164 A1 | 3/2009 | Segal et al. |
| 2009/0117617 A1 | 5/2009 | Holmes et al. |
| 2010/0177983 A1 | 7/2010 | Hsu |
| 2010/0218264 A1 | 8/2010 | Cui et al. |
| 2011/0041195 A1 | 2/2011 | Doyon |
| 2011/0189776 A1 | 8/2011 | Terns et al. |
| 2011/0201055 A1 | 8/2011 | Doyon et al. |
| 2011/0301073 A1 | 12/2011 | Gregory et al. |
| 2012/0128635 A1 | 5/2012 | Gregory et al. |
| 2013/0122591 A1 | 5/2013 | Cost et al. |
| 2013/0137104 A1 | 5/2013 | Cost et al. |
| 2013/0177960 A1 | 7/2013 | Rebar |

FOREIGN PATENT DOCUMENTS

| | | |
|---|---|---|
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/007752 A2 | 1/2002 |
| WO | WO 02/016536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 2007/014275 A2 | 2/2007 |
| WO | WO 2010/079430 A1 | 7/2010 |
| WO | WO 2010/117464 A1 | 10/2010 |
| WO | WO 2011/011767 A1 | 1/2011 |
| WO | WO 2011/097036 A1 | 8/2011 |
| WO | WO 2011/100058 A1 | 8/2011 |
| WO | WO 2012/015938 A2 | 2/2012 |
| WO | WO 2013/044008 A2 | 3/2013 |
| WO | WO 2014/093622 A2 | 6/2014 |

OTHER PUBLICATIONS

Beerli, et al., "Engineering Polydactyl Zinc-Finger Transcription Factors," *Nature Biotechnol* 20:135-141(2002).
Beumer, et al., "Efficient Gene Targeting in *Drosophila* With Zinc-Finger Nucleases," *Genetics* 172:2391-2403 (2006).
Bibikova, et al., "Stimulation of Homologous Recombination Through Targeted Cleavage by Chimeric Nucleases," *Mol. Cellular Biol.* 21(1):289-297 (2001).
Bitinaite, et al., "FOK I Dimerization Is Required for DNA Cleavage," *PNAS USA* 95:10570-10575 (1998).
Boch, et al., "Breaking the Code of DNA Binding Specificity of TAL-Type III Effectors," *Science* 326:1509-1512 (2009).
Bonas, et al., "Genetic and Structural Characterization of the Avirulence Gene AVRBS3 From *Xanthomonas campestris* Pv. *vesicatoria*," *Mol. Gen. Genet.* 218:127-136 (1989).
Carbery, et al., "Targeted Genome Modification in Mice Using Zinc-Finger Nucleases" *Genetics* 186:451-459 (2010).
Choo, et al., "Advances in Zinc Finger Engineering," *Curr. Opin. Biotechnol.* 12:632-637 (2000).
Christian, et al., "Targeting DNA Double-Strand Breaks With TAL Effector Nucleases," *Genetics* 186:757-761 (2010).

Cohen-Tannoudji, et al., "I-SCEI-Induced Gene Replacement at a Natural Locus in Embryonic Stem Cells" *Mol. Cell. Biol.* 18:1444-1448 (1998).
Cong, et al., "Multiplex Genome Engineering Using CRISPR/CAS Systems," *Science* 339(6121):819-823.
Dagnino, et al., "Molecular Diagnosis of Analbuminemia: A New Case Caused by a Nonsense Mutation in the Albumin Gene," *International Journal of Molecular Sciences*, 12(12):7314-7322 (2011).
Deonarain, Mahendra P., "Ligand-Targeted Receptor-Mediated Vectors for Gene Delivery," *Expert Opin. Ther. Pat.* 8:53-69 (1998).
DiCarlo, et al., "Genome Engineering in *Saccharomyces cerevisiae* Using CRISPR-CAS Systems," *Nuc. Acid. Res.* Doi:10.1093 (2013).
Donoho, et al., "Analysis of Gene Targeting and Intrachromosomal Homologous Recombination Stimulated by Genomic Double-Strand Breaks in Mouse Embryonic Stem Cells, *Mol. Cell. Biol.* 18(7):4070-4078 (1998).
Doyon, et al., "Heritable Targeted Gene Disruption in Zebrafish Using Designed Zinc-Finger Nucleases" *Nature Biotech.*, 26(6):702-708 (2008).
Edelstein, et al., "Gene Therapy Clinical Trials Worldwide 1989-2004—An Overview," *Journal Gene Med.* 6:597-602 (2004).
Gabathuler, et al., "Approaches to Transport Therapeutic Drugs Across the Blood-Brain Barrier to Treat Brain Diseases," *Neurobiology of Disease* 37:48-57 (2010).
Geurts, et al., "Knockout Rats Via Embryo Microinjection of Zinc-Finger Nucleases," *Science* 325:433 (2009).
Grabowski, et al., "Phenotype, Diagnosis, and Treatment of Gaucher's Disease," 372(9645):1263-1271 (2008).
Guschin, et al., "A Rapid and General Assay for Monitoring Endogenous Gene Modification," *Methods Mol. Biol.* 649:247-256 (2010).
Hauschild, et al., "Efficient Generation of a Biallelic Knockout in Pigs Using Zinc-Finger Nucleases," *PNAS* 108(29):12013-12017 (2011).
Heuer, et al., "Repeat Domain Diversity of AVRBS3-Like Genes in Ralstonia Solanacearum Strains and Association With Host Preferences in the Field" *Appl. and Envir. Micro.* 73(13):4379-4384 (2007).
High, Katherine A., "The Moving Finger," *Nature* 435:577-578 (2005).
Isalan, et al., "A Rapid, Generally Applicable Method to Engineer Zinc Fingers Illustrated by Targeting the HIV-1 Promoter," *Nat. Biotechnol.* 19:656-660 (2001).
Jinek, et al., "RNA-Programmed Genome Editing in Human Cells," *eLife* 2:e00471 (2013).
Jinek, et al., "A Programmable Dual-RNA-Guided DNA Endonuclease in Adaptive Bacterial Immunity," *Science* 337:816-821 (2012).
Johnson-Saliba, et al., "Gene Therapy: Optimising DNA Delivery to the Nucleus," *Curr. Drug. Targets*, 2:371-399 (2001).
Kay, et al., "A Bacterial Effector Acts as a Plant Transcription Factor and Induces a Cell Size Regulator," *Science* 318:648-651 (2007).
Kim, et al., "Insertion and Deletion Mutants of FOKI Restriction Endonuclease," *J. Biol. Chem.* 269:31978-31982 (1994b).
Kim, et al., "Chimeric Restriction Endonuclease," *PNAS USA* 91:883-887 (1994a).
Kim, et al., "Hybrid Restriction Enzymes: Zinc Finger Fusions to FOK I Cleavage Domain," *PNAS USA* 93(3):1156-1160 (1996).
Krall, et al., "Cells Expressing Human Glucocerebrosidase From a Retroviral Vector Repopulate Macrophages and Central Nervous System Microglia After Murine Bone Marrow Transplantation," *Blood* 83(9):2737-2748 (1994).
Li, et al., "Functional Domains in FOK I Restriction Endonuclease," *PNAS USA* 89:4275-4279 (1992).
Li, et al., "Alteration of the Cleavage Distance of FOK I Restriction Endonuclease by Insertion Mutagenesis," *PNAS USA* 90:2764-2768 (1993).
Li, et al., "In Vivo Genome Editing Restores Haemostasis in a Mouse Model of Haemophilia," *Nature* 475(7355):217-222 (2011).
Luo, et al., "Synthetic DNA Delivery Systems," *Nature Biotechnol.* 18:33-37 (2000).

(56) References Cited

OTHER PUBLICATIONS

Meng, et al., "Targeted Gene Inactivation in Zebrafish Using Engineered Zinc Finger Nucleases," *Nature Biotechnology* 26(6):695-701 (2008).
Morton, et al., "Induction and Repair of Zinc-Finger Nuclease-Targeted Double-Strand Breaks in Caenorhabditis Elegans Somatic Cells" *PNAS* 13(44):16370-16375 (2006).
Moscou, et al., "A Simple Cipher Governs DNA Recognition by TAL Effectors," *Science* 326:1501 (2009).
O'Neill, et al., "Comparison of the Chromosomal Localization of Murine and Human Glucocerebrosidase Genes and of the Deduced Amino Acid Sequences," *PNAS* 86: 5049-5053 (2004).
Pabo, et al., "Design and Selection of Novel CYS2HIS2 Zinc Finger Proteins," *Ann. Rev. Biochem.* 70:313-340 (2001).
Palù, et al., "In Pursuit of New Developments for Gene Therapy of Human Diseases," *J. Biotechnol.* 68:1-13 (1999).
Perez, et al., "Establishment of HIV-1 Resistance in CD4+ T Cells by Genome Editing Using Zinc-Finger Nucleases," *Nature Biotechnology* 26(7):808-816 (2008).
Pfeifer, et al., "Gene Therapy: Promises and Problems," *Annu. Rev. Genomics. Hum. Genet.* 2:177-211 (2001).
Ponder, Katherine P., "Immune Response Hinders Therapy for Lysosomal Storage Diseases," *J. Clin. Invest.* 118(8):2686 (2008).
Porteus, et al., "Gene Targeting Using Zinc Finger Nucleases," *Nature Biotechnology*, 23(8):967-973 (2005).
Qi, et al., "Repurposing Crispr as an RNA-Guided Platform for Sequence-Specific Control of Gene Expression," *Cell* 152:1173-1183 (2013).
Ramirez, et al., "Unexpected Failure Rates for Modular Assembly of Engineered Zinc Fingers," *Nature Methods* 5(5):374-375, plus supplemental material (2008).
Roberts, et al., "Rebase: Restriction Enzymes and Methyltransferases," *Nucleic Acid Research* 31:418-420 (2003).
Schornack, et al., "Gene-For-Gene-Mediated Recognition of Nuclear-Targeted AVRBS3-Like Bacterial Effector Proteins," *J Plant Physiol.* 163(3):256-272 (2006).
Segal, et al., "Custom DNA-Binding Proteins Come of Age: Polydactyl Zinc-Finger Proteins," *Curr. Opin. Biotechnol.* 12:632-637 (2001).
Segal, David J., "Bacteria Herald a New Era of Gene Editing," *eLife* 2:e00563 (2013).
Shoji, et al., "Current Status of Delivery Systems to Improve Target Efficacy of Oligonucleotides," *Current Pharmaceutical Design* 10:785-796 (2004).
Swarts, et al., CRISPR Interfernce Directs Strand Specific Spacer Acquisition, *PLos One* 7(4):e35888 (2012).
Tybulewicz, et al., "Animal Model of Gaucher's Disease From Targeted Disruption of the Mouse Glucocerebrosidase Gene," *Letters to Nature* 357:407-410 (1992).
Urnov, et al., "Highly Efficient Endogenous Human Gene Correction Using Designed Zinc-Finger Nucleases," *Nature* 435(7042):646-651 (2005).
Vasquez, et al. "Manipulating the Mammalian Genome by Homologous Recombination," *PNAS* 98(15): 8403-8410 (2001).
Verma, et al., "Gene Therapy—Promises, Problems and Prospects," *Nature* 389:239-242 (1997).
Wikipedia, "Lysosomal Storage Diseases," http://en.wikipedia.org/wiki/Lysosomal_Storage_Disease, 8 pgs. (2014).
Wikipedia, "Gaucher's Disease," http://en.wikopedia.org/wiki/Gaucher's_disease, 8 pgs. (2014).
Yang, et al., "Purification, Cloning, and Characterization of the CEL I Nuclease," *Biochemistry* 39:3533-3541 (2000).
Anguela, et al., "In Vivo Genome Editing of Liver Albumin for Therapeutic Gene Expression: Rescue of Hemophilic Mice via Integration of Factor 9," Blood, vol. 120, No. 21, 5 pages (2012).
Mali, et al., "RNA-Guided Human Genome Engineering via Cas9," Science, vol. 339, No. 6121, pp. 823-826 (2013).

\* cited by examiner

METHODS AND COMPOSITIONS FOR THE TREATMENT OF LYSOSOMAL STORAGE DISEASES

CROSS-REFERENCE TO RELATED APPLICATIONS

The present application is a continuation of U.S. patent application Ser. No. 13/839,336, filed Mar. 15, 2013, which claims the benefit of U.S. Provisional Application No. 61/670,463, filed Jul. 11, 2012 and U.S. Provisional Application No. 61/704,072, filed Sep. 21, 2012, the disclosures of which are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, created on Nov. 17, 2017, is named 8325-0097-01_SL.txt and is 28,045 bytes in size.

TECHNICAL FIELD

The present disclosure is in the field of the treatment of Lysosomal storage diseases (LSDs) and gene therapy.

BACKGROUND

Gene therapy holds enormous potential for a new era of human therapeutics. These methodologies will allow treatment for conditions that heretofore have not been addressable by standard medical practice. One area that is especially promising is the ability to add a transgene to a cell to cause that cell to express a product that previously not being produced in that cell. Examples of uses of this technology include the insertion of a gene encoding a therapeutic protein, insertion of a coding sequence encoding a protein that is somehow lacking in the cell or in the individual and insertion of a sequence that encodes a structural nucleic acid such as a microRNA.

Transgenes can be delivered to a cell by a variety of ways, such that the transgene becomes integrated into the cell's own genome and is maintained there. In recent years, a strategy for transgene integration has been developed that uses cleavage with site-specific nucleases for targeted insertion into a chosen genomic locus (see, e.g., co-owned U.S. Pat. No. 7,888,121). Nucleases, such as zinc finger nucleases (ZFNs), transcription activator-like effector nucleases (TALENs), or nuclease systems such as the CRISPR/Cas system (utilizing an engineered guide RNA), are specific for targeted genes and can be utilized such that the transgene construct is inserted by either homology directed repair (HDR) or by end capture during non-homologous end joining (NHEJ) driven processes.

Targeted loci include "safe harbor" loci such as the AAVS1, HPRT and CCR5 genes in human cells, and Rosa26 in murine cells (see, e.g., co-owned U.S. Patent Publication Nos. 2008/0299580; 2008/0159996 and 2010/00218264 and U.S. Pat. No. 9,222,105). Nuclease-mediated integration offers the prospect of improved transgene expression, increased safety and expressional durability, as compared to classic integration approaches that rely on random integration of the transgene, since it allows exact transgene positioning for a minimal risk of gene silencing or activation of nearby oncogenes.

While delivery of the transgene to the target cell is one hurdle that must be overcome to fully enact this technology, another issue that must be conquered is insuring that after the transgene is inserted into the cell and is expressed, the gene product so encoded must reach the necessary location with the organism, and be made in sufficient local concentrations to be efficacious. For diseases characterized by the lack of a protein or by the presence of an aberrant non-functional one, delivery of a transgene encoded wild type protein can be extremely helpful.

Lysosomal storage diseases (LSDs) are a group of rare metabolic monogenic diseases characterized by the lack of functional individual lysosomal proteins normally involved in the breakdown of waste lipids, glycoproteins and mucopolysaccharides. These diseases are characterized by a buildup of these compounds in the cell since it is unable to process them for recycling due to the mis-functioning of a specific enzyme. The most common examples are Gaucher's (glucocerebrosidase deficiency—gene name: GBA), Fabry's (α galactosidase deficiency—GLA), Hunter's (iduronate-2-sulfatase deficiency-IDS), Hurler's (alpha-L iduronidase deficiency—IDUA), and Niemann-Pick's (sphingomyelin phosphodiesterase 1deficiency—SMPD1) diseases. When grouped all together, LSDs have an incidence in the population of about 1 in 7000 births. These diseases have devastating effects on those afflicted with them. They are usually first diagnosed in babies who may have characteristic facial and body growth patterns and may have moderate to severe mental retardation. Treatment options include enzyme replacement therapy (ERT) where the missing enzyme is given to the patient, usually through intravenous injection in large doses. Such treatment is only to treat the symptoms and is not curative, thus the patient must be given repeated dosing of these proteins for the rest of their lives, and potentially may develop neutralizing antibodies to the injected protein. Often these proteins have a short serum half life, and so the patient must also endure frequent infusions of the protein. For example, Gaucher's disease patients receiving the Cerezyme® product (imiglucerase) must have infusions three times per week. Production and purification of the enzymes is also problematic, and so the treatments are very costly (>$100,000 per year per patient).

Thus, there remains a need for additional methods and compositions that can be used to treat a monogenic disease (e.g. Lysosomal storage diseases) through genome editing, and methods to deliver an expressed transgene encoded gene product at a therapeutically relevant level.

SUMMARY

Disclosed herein are methods and compositions for treating a monogenic disease. The invention describes methods for insertion of a transgene sequence into a suitable target cell wherein the transgene encodes a protein that treats the disease. The therapeutic protein may be excreted from the target cell such that it is able to affect or be taken up by other cells that do not harbor the transgene. The invention also provides for methods for the production of a cell (e.g., a mature or undifferentiated cell) that produces high levels of a therapeutic where the introduction of a population of these altered cells into a patient will supply that needed protein to treat a disease or condition.

In one aspect, described herein is a zinc-finger protein (ZFP) that binds to target site in a region of interest (e.g., a disease associated gene, a highly expressed gene, an albumin gene or other or safe harbor gene) in a genome, wherein the ZFP comprises one or more engineered zinc-finger binding domains. In one embodiment, the ZFP is a zinc-finger nuclease (ZFN) that cleaves a target genomic region of interest, wherein the ZFN comprises one or more engineered zinc-finger binding domains and a nuclease cleavage domain or cleavage half-domain. Cleavage domains and cleavage half domains can be obtained, for example, from various restriction endonucleases and/or homing endonucleases. In one embodiment, the cleavage half-domains are derived from a Type IIS restriction endonuclease (e.g., Fok I). In certain embodiments, the zinc finger domain recognizes a target site in a disease associated or safe harbor gene such as albumin (e.g., a zinc finger protein having 5 or 6 fingers with the recognition helix regions shown in a single row of Table 3).

In another aspect, described herein is a TALE protein (Transcription activator like) that binds to target site in a region of interest (e.g., a highly expressed gene, a disease associated gene or a safe harbor gene) in a genome, wherein the TALE comprises one or more engineered TALE binding domains. In one embodiment, the TALE is a nuclease (TALEN) that cleaves a target genomic region of interest, wherein the TALEN comprises one or more engineered TALE DNA binding domains and a nuclease cleavage domain or cleavage half-domain. Cleavage domains and cleavage half domains can be obtained, for example, from various restriction endonucleases and/or homing endonucleases. In one embodiment, the cleavage half-domains are derived from a Type IIS restriction endonuclease (e.g., Fok I). In certain embodiments, the TALE DNA binding domain recognizes a target site in a highly expressed, disease associated, or safe harbor gene.

In another aspect, described herein is a CRISPR/Cas system that binds to target site in a region of interest (e.g., a highly expressed gene, a disease associated gene or a safe harbor gene) in a genome, wherein the CRISPR/Cas system comprises a CRIPSR/Cas nuclease and an engineered crRNA/tracrRNA (or single guide RNA). In certain embodiments, the CRISPR/Cas system recognizes a target site in a highly expressed, disease associated, or safe harbor gene.

The ZFN, TALEN, and/or CRISPR/Cas system as described herein may bind to and/or cleave the region of interest in a coding or non-coding region within or adjacent to the gene, such as, for example, a leader sequence, trailer sequence or intron, or within a non-transcribed region, either upstream or downstream of the coding region. In certain embodiments, the ZFN, TALEN, and/or CRISPR/Cas system binds to and/or cleaves a highly expressed gene, for example a globin gene in red blood cells (RBCs). See, e.g., U.S. Provisional Patent Application No. 61/670,451, titled "Methods and Compositions for Delivery of Biologics," filed Jul. 11, 2012, incorporated by reference in its entirety herein. In other embodiments, the ZFN, TALEN, and/or CRISPR/Cas system binds to and/or cleaves a safe-harbor gene, for example a CCR5 gene, a PPP1R12C (also known as AAV S1) gene, albumin, HPRT or a Rosa gene. See, e.g., U.S. Pat. No. 9,222,105, U.S. Patent Publication Nos. 2008/0299580; 2008/0159996 and 2010/00218264; and U.S. Provisional Patent Application Nos. 61/537,349, 61/560,506, 61/670,451 titled "Methods and Compositions for Regulation of Transgene Expression" filed Jul. 11, 2012 and incorporated by reference herein. In addition, to aid in selection, the HPRT locus may be used (see U.S. Pat. Nos. 8,895,264 and 9,222,105). In other embodiments, the ZFN, TALEN, and/or CRISPR/Cas system may bind to and/or cleave a disease associated gene (e.g. the gene encoding lysosomal hydrolase α-galactosidase A (AGA), related to Fabry's Disease). In another aspect, described herein are compositions comprising one or more of the zinc-finger and/or TALE nucleases or CRISPR/Cas system described herein. Also described are compositions comprising the one or more of these nucleases and donor nucleic acid. In some aspects, described are engineered nucleases or CRISPR/Cas systems capable of cleaving disease associate aberrant regulatory genes and methods of using these nucleases to treat the disease by reducing or eliminating expression of the aberrant gene product.

In one aspect, the invention describes a method of treating a lysosomal storage disease by inserting in a corrective transgene into a suitable target cell (e.g., blood cell, liver cell, brain cell, stem cell, precursor cell, etc.) such that the product encoded by that corrective transgene is expressed. In one embodiment, the corrective transgene is inserted into a cell line for the in vitro production of the replacement protein. The cells comprising the transgene or the protein produced by the cells can be used to treat a patient in need thereof, for example following purification of the produced protein. In another embodiment, the corrective transgene is inserted into a target tissue in the body such that the replacement protein is produced in vivo. In some aspects, the expressed protein is excreted from the cell to act on or be taken up by other cells (e.g. via exportation into the blood) that lack the transgene. In some instances, the target tissue is the liver. In other instances, the target tissue is the brain. In other instances, the target is blood (e.g., vasculature). In other instances, the target is skeletal muscle. In one embodiment, the corrective gene comprises the wild type sequence of the functioning gene, while in other embodiments, the sequence of the corrective transgene is altered in some manner to give enhanced biological activity. In some aspects, the corrective transgene comprises optimized codons to increase biological activity, while in other aspects, the sequence is altered to give the resultant protein more desired function (e.g., improvement in stability, alteration of charge to alter substrate binding etc.). In some embodiments, the transgene is altered for reduced immunogenicity. In other cases, the transgene is altered such that the encoded protein becomes a substrate for transporter-mediated delivery in specific tissues such as the brain (see Gabathuler, et al., (2010) *Neurobiology of Disease* 37: 48-57).

In another aspect, the invention supplies an engineered nuclease protein capable of cleaving (editing) the genome of a stem or precursor cell (e.g., blood cell precursor, liver stem cell, etc.) for introduction of a desired transgene. In some aspects, the edited stem or precursor cells are then expanded and may be induced to differentiate into a mature edited cells ex vivo, and then the cells are given to the patient. In other aspects, the edited precursors (e.g., CD34+ stem cells) are given in a bone marrow transplant which, following successful implantation, proliferate producing edited cells that then differentiate and mature in vivo and contain the biologic expressed from the transgene. In other aspects, the edited stem cells are muscle stem cells which are then introduced into muscle tissue. In some aspects, the engineered nuclease is a Zinc Finger Nuclease (ZFN) and in others, the nuclease is a TALE nuclease (TALEN), and in other aspects, a CRISPR/Cas system is used. The nucleases may be engineered to have specificity for a safe harbor locus, a gene associated with a disease, or for a gene that is highly expressed in cells. By way of non-limiting example only, the safe harbor locus may be the AAVS1 site, the CCR5 gene, albumin or the HPRT gene while the disease associated gene may be the GLA gene encoding lysosomal hydrolase α-galactosidase A (See Table 2). By way of non-limiting example only, a gene that is highly expressed in red blood cells (RBCs) is beta-globin. In another aspect, the transgenic cells are sensitized ex vivo via electrosensitization to increase their susceptibility for disruption following exposure to an energy source (e.g. ultrasound) (see International Patent Publication No. WO 2002/007752).

In another aspect, described herein is a polynucleotide encoding one or more ZFN, TALEN, and/or CRISPR/Cas system described herein. The polynucleotide may be, for example, mRNA. In some aspects, the mRNA may be chemically modified (See e.g. Kormann, et al., (2011) *Nature Biotechnology* 29(2): 154-157).

In another aspect, described herein is a ZFN, TALEN, and/or CRISPR/Cas system expression vector comprising a polynucleotide, encoding one or more ZFN, TALEN, and/or CRISPR/Cas system described herein, operably linked to a promoter. In one embodiment, the expression vector is a viral vector.

In another aspect, described herein is a host cell comprising one or more ZFN, TALEN, and/or CRISPR/Cas system expression vectors as described herein. The host cell may be stably transformed or transiently transfected or a combination thereof with one or more ZFN, TALEN, and/or CRISPR/Cas system expression vectors. In some embodiments, the host cell is a liver cell.

In another aspect, described herein is a method for cleaving a highly expressed, disease associated and/or safe harbor locus in a cell, the method comprising: introducing, into the cell, one or more polynucleotides encoding one or more ZFN, TALEN, and/or CRISPR/Cas system that bind(s) to a target site in the one or more target loci under conditions such that the ZFN(s), TALEN(s) or CRIPSR/Cas system is (are) expressed and the one or more loci are cleaved. Non-limiting examples of ZFN, TALEN, and/or CRISPR/Cas systems that bind to highly expressed and/or safe harbor loci are disclosed in U.S. Patent Publication Nos. 2008/0299580; 2008/0159996; and 2010/00218264 and U.S. Pat. Nos. 9,222,105; 8,895,264; 9,394,545; and 9,150,847 and U.S. Provisional Patent Application No. 61/670,451, titled "Methods and Compositions for Delivery of Biologics,", all of which are incorporated by reference in their entireties herein.

In other embodiments, a genomic sequence in any target gene is replaced with the therapeutic transgene, for example using a ZFN, TALEN, and/or CRISPR/Cas system (or vector encoding said ZFN, TALEN, and/or CRISPR/Cas system) as described herein and a "donor" sequence or transgene that is inserted into the gene following targeted cleavage with the the ZFN, TALEN, and/or CRISPR/Cas system. The donor sequence may be present in the ZFN or TALEN vector, present in a separate vector (e.g., Ad, AAV or LV vector) or, alternatively, may be introduced into the cell using a different nucleic acid delivery mechanism. Such insertion of a donor nucleotide sequence into the target locus (e.g., highly expressed gene, disease associated gene, other safe-harbor gene, etc.) results in the expression of the transgene under control of the target locus's (e.g., albumin, globin, etc.) endogenous genetic control elements. In some aspects, insertion of the transgene of interest, for example into a target gene (e.g., albumin), results in expression of an intact exogenous protein sequence and lacks any amino acids encoded by the target (e.g., albumin). In other aspects, the expressed exogenous protein is a fusion protein and comprises amino acids encoded by the transgene and by the endogenous locus into which the transgene is inserted (e.g., from the endogenous target locus or, alternatively from sequences on the transgene that encode sequences of the target locus). The target may be any gene, for example, a safe harbor gene such as an albumin gene, an AAVS1 gene, an HPRT gene; a CCR5 gene; or a highly expressed gene such as a globin gene in an RBC (e.g., beta globin or gamma globin). In some instances, the endogenous sequences will be present on the amino (N)-terminal portion of the exogenous protein, while in others, the endogenous sequences will be present on the carboxy (C)-terminal portion of the exogenous protein. In other instances, endogenous sequences will be present on both the N- and C-terminal portions of the exogenous protein. The endogenous sequences may include full-length wild-type or mutant endogenous sequences or, alternatively, may include partial endogenous amino acid sequences. In some embodiments, the endogenous gene-transgene fusion is located at the endogenous locus within the cell while in other embodiments, the endogenous sequence-transgene coding sequence is inserted into another locus within a genome (e.g., a IDUA-transgene sequence inserted into an albumin, HPRT or CCR5 locus). In some aspects, the safe harbor is selected from the AAVS1, Rosa, albumin, HPRT or CCR5 locus (see co-owned U.S. Patent Publication Nos. 2008/0299580; 2008/0159996; and 2010/00218264 and U.S. Pat. Nos. 9,222,105; 8,895,264; 9,394,545; and 9,150,847 and U.S. Provisional Patent Application No. 61/670,451, titled "Methods and Compositions for Regulation of Transgene Expression" filed Jul. 11, 2011). In other embodiments, the disease associated gene is selected from GLA (lysosomal hydrolase α-galactosidase A), or from one or more genes listed in Table 2.

In some embodiments the transgene is expressed such that a therapeutic protein product is retained within the cell (e.g., precursor or mature cell). In other embodiments, the transgene is fused to the extracellular domain of a membrane protein such that upon expression, a transgene fusion will result in the surface localization of the therapeutic protein. In some aspects, the extracellular domain is chosen from those proteins listed in Table 1. In some aspects, the edited cells also comprise a transmembrane protein to traffic the cells to a particular tissue type. In one aspect, the transmemberane protein is a antibody, while in others, the transmembrane protein is a receptor. In certain embodiments, the cell is a precursor (e.g., CD34+ or hematopoietic stem cell) or mature RBC. In some aspects, the therapeutic protein product encoded on the transgene is exported out of the cell to affect or be taken up by cells lacking the transgene. In certain embodiments, the cell is a liver cell which releases the therapeutic protein into the blood stream to act on distal tissues (e.g., brain).

The invention also supplies methods and compositions for the production of a cell (e.g., RBC) carrying a therapeutic protein for an LSD that can be used universally for all patients as an allogenic product. This would allow the development of a single product for the treatment of patients with a particular LSD, for example. These carriers may comprise transmembrane proteins to assist in the trafficking of the cell. In one aspect, the transmemberane protein is an antibody, while in others, the transmembrane protein is a receptor.

In one aspect, the invention provides methods and compositions for the knockout of disease associated genes. In some embodiments, these genes are those whose products may regulate expression of a gene in precursor or mature cell. In some aspects, the knock out is to the regulatory target site on the DNA for such proteins. In some aspects, the regulator gene is aberrant such that knock out of the gene restores normal function. In other aspects, the gene to be knocked out is a disease associated allele such that the knocking out of this diseased allele allows expression from a wild type allele and restores normal function.

In one embodiment, the transgene is expressed from the albumin promoter following insertion into the albumin locus. The biologic encoded by the transgene then may be released into the blood stream if the transgene is inserted into a hepatocyte in vivo. In some aspects, the transgene is delivered to the liver in vivo in a viral vector through intravenous injection.

In another embodiment, the transgene encodes a non-coding RNA, e.g. an shRNA. Expression of the transgene prior to cell maturation will result in a cell containing the non-coding RNA of interest.

In another embodiment, the invention describes precursor cells (hematopoietic stem cells, muscle stem cells or CD34+ hematopoietic stem cell (HSC) cells) into which a transgene has been inserted such that mature cells derived from these precursors contain high levels of the product encoded by the transgene. In some embodiments, these precursors are induced pluripotent stem cells (iPSC).

In some embodiments, the methods of the invention may be used in vivo in transgenic animal systems. In some aspects, the transgenic animal may used in model development where the transgene encodes a human gene. In some instances, the transgenic animal may be knocked out at the corresponding endogenous locus, allowing the development of an in vivo system where the human protein may be studied in isolation. Such transgenic models may be used for screening purposes to identify small molecules, or large biomolecules or other entities which may interact with or modify the human protein of interest. In some aspects, the transgene is integrated into the selected locus (e.g., highly expressed or safe-harbor) into a stem cell (e.g., an embryonic stem cell, an induced pluripotent stem cell, a hepatic stem cell, a neural stem cell etc.) or animal embryo obtained by any of the methods described herein, and then the embryo is implanted such that a live animal is born. The animal is then raised to sexual maturity and allowed to produce offspring wherein at least some of the offspring comprise the integrated transgene.

In a still further aspect, provided herein is a method for site specific integration of a nucleic acid sequence into an endogenous locus (e.g., disease-associated, highly expressed such as globin in RBCs, or safe harbor gene such as albumin, CCR5, HPRT or Rosa gene) of a chromosome, for example into the chromosome of an embryo. In certain embodiments, the method comprises: (a) injecting an embryo with (i) at least one DNA vector, wherein the DNA vector comprises an upstream sequence and a downstream sequence flanking the nucleic acid sequence to be integrated, and (ii) at least one RNA molecule encoding a zinc finger, TALE nuclease or CRISPR/Cas system that recognizes the site of integration in the target locus, and (b) culturing the embryo to allow expression of the ZFN, TALEN, and/or CRISPR/Cas system, wherein a double stranded break introduced into the site of integration by the ZFN, TALEN, and/or CRISPR/Cas system is repaired, via homologous recombination with the DNA vector, so as to integrate the nucleic acid sequence into the chromosome.

In any of the previous embodiments, the methods and compounds of the invention may be combined with other therapeutic agents for the treatment of subjects with lysosomal storage diseases. In some aspects, the methods and compositions are used in combination with methods and compositions to allow passage across the blood brain barrier. In other aspects, the methods and compositions are used in combination with compounds known to suppress the immune response of the subject.

A kit, comprising the ZFN, TALEN, and/or CRISPR/Cas system of the invention, is also provided. The kit may comprise nucleic acids encoding the ZFN, TALEN, and/or CRISPR/Cas system, (e.g. RNA molecules or the ZFN, TALEN, and/or CRISPR/Cas system encoding genes contained in a suitable expression vector), donor molecules, expression vectors encoding the single guide RNA suitable host cell lines, instructions for performing the methods of the invention, and the like.

These and other aspects will be readily apparent to the skilled artisan in light of disclosure as a whole.

BRIEF DESCRIPTION OF THE DRAWINGS

FIG. 1A shows the results measured when the transfection of the albumin-specific nuclease pairs into Neuro2A cells was carried out at 37° C. and FIG. 1B shows results when transduction of nuclease pairs under hypothermic shock (30° C.). The percent mismatch, or % indels, is a measure of the nuclease activity of each pair under each condition.

FIG. 3A depicts a gel with the Cel-I results from mice given AAV2/8 containing a GFP expression cassette or AAV2/8 comprising the ZFNs, where the AAV were produced via a 293 expression system or a baculovirus system. FIG. 3B depicts the quantitation of the lanes on the gel and shows that infection of the mice with the AAV containing the albumin specific ZFNs results in nearly 30% quantitatable NHEJ activity.

FIG. 4A shows a Western blot against the huGLa protein encoded by the transgene, where the arrow indicates the presumed protein. Comparison of the mouse samples from those mice that received both ZFN and donor (samples 1-1, 1-2 and 1-3)

with the samples that either received only ZFN (4-1, 4-2, 4-3) or those that only received the huGLa donor ("hu Fabry donor"), samples 5-1 and 5-2 leads to identification of a band that coincides with the human liver lysate control. FIG. 4B depicts ELISA results using a huGLa specific ELISA kit, where samples were analyzed from mice either 14 or 30 days following virus introduction. Error bars represent standard deviations (n=3). The results demonstrate that the mice that received both the ZFN and donor (circles) had higher amounts of huGLa signal that those that only received ZFN (squares) or only received donor (triangles).

FIG. 5A shows the results using the IDUA encoding transgene, FIG. 5B shows the results using the GLA transgene, FIG. 5C shows the results using the IDS transgene, and FIG. 5D shows the results using the GBA transgene.

FIG. 6 also depicts the location of the two PCR primers ("mALB-OOF1" and "Acc651-SA-rev-sh") used to detect the type of integration that has occurred.

FIG. 7A depicts the mice with the IDUA transgene, FIG. 7B depicts those with the GLA transgene, and FIG. 7C depicts those with the IDS transgene. In all cases, the bands indicate that insertion of the transgenes has occurred through both NHEJ-mediated and HDR-mediated integration.

FIG. 9A shows that integration occurred through both NHEJ-mediated and HDR-mediated integration for the targeted GLA, IDUA and IDS transgene.

FIG. 9B shows the same for the GBA transgene.

DETAILED DESCRIPTION

Figures 1A, 1B:
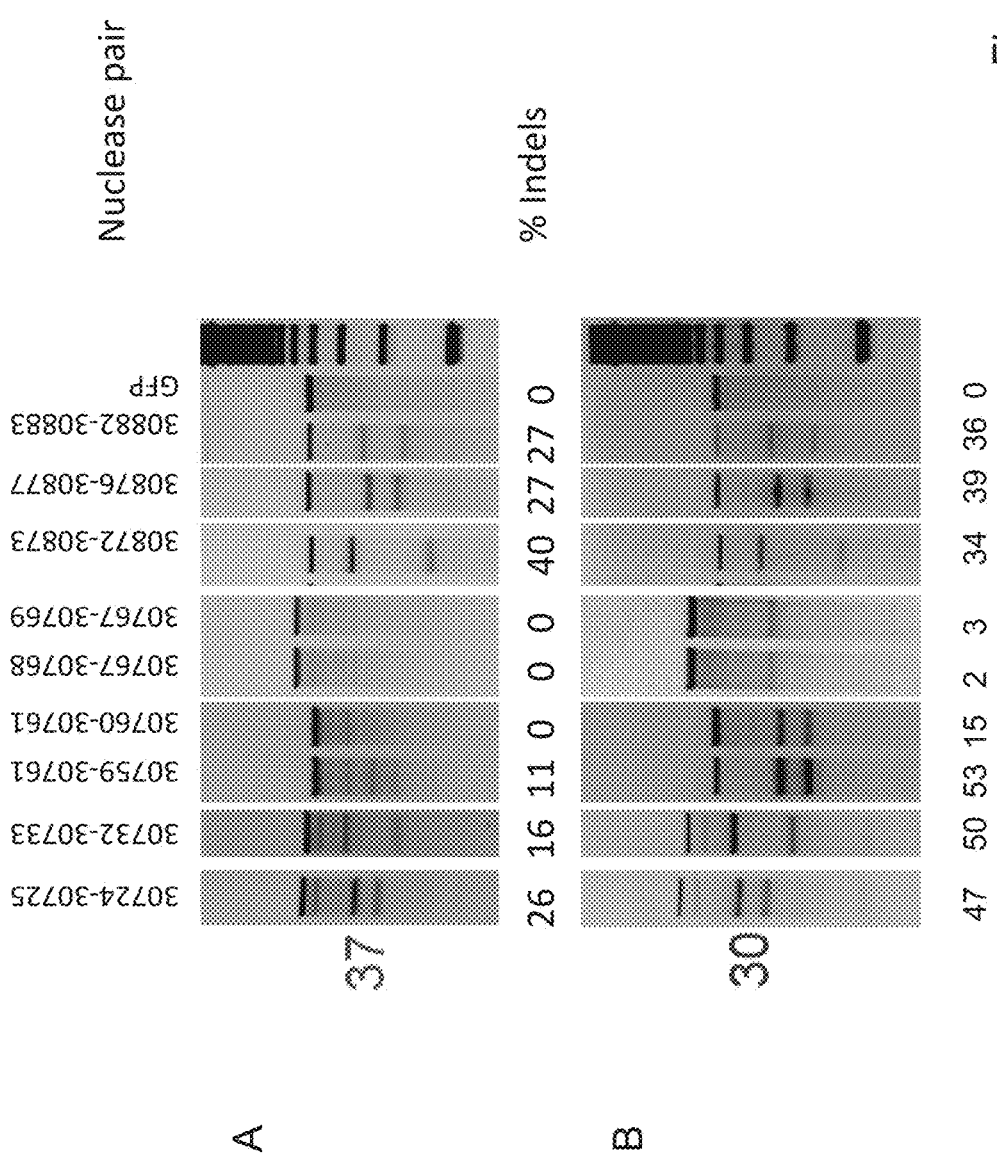
FIGS. 1A and 1B depict a composite set of gels demonstrating the results of a Cel-I mismatch assay (Surveyor™, Transgenomic) that measures cleavage at a location of interest by a nuclease pair that has been followed by an NHEJ event. NHEJ causes the insertion or deletion of nucleotide bases ("indels") which then creates a mismatch when the DNA strand is annealed with a wild-type DNA strand.

Disclosed herein are methods and compositions for treating or preventing a lysosomal storage disease (LSD). The invention provides methods and compositions for insertion of a gene encoding a protein that is lacking or insufficiently expressed in the subject with the LSD such that the gene is expressed in the liver and the therapeutic (replacement) protein is expressed. The invention also describes the alteration of a cell (e.g., precursor or mature RBC, iPSC or liver cell) such that it produces high levels of the therapeutic and the introduction of a population of these altered cells into a patient will supply that needed protein. The transgene can encode a desired protein or structural RNA that is beneficial therapeutically in a patient in need thereof.

Thus, the methods and compositions of the invention can be used to express from a transgene therapeutically beneficial proteins from any locus (e.g., highly expressed albumin locus) to replace enzymes that are defective in lysosomal storage diseases. Additionally, the invention provides methods and compositions for treatment of these diseases by insertion of the sequences into highly expressed loci in cells such as liver cells.

In addition, the transgene can be introduced into patient derived cells, e.g. patient derived induced pluripotent stem cells (iPSCs) or other types of stems cells (embryonic or hematopoietic) for use in eventual implantation. Particularly useful is the insertion of the disease associated transgene into a hematopoietic stem cell for implantation into a patient in need thereof. As the stem cells differentiate into mature cells, they will contain high levels of the replacement protein for delivery to the tissues.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also International Patent Publication Nos. WO 98/53058; WO 98/53059; WO 98/53060; WO 02/016536; and WO 03/016496 and U.S. Patent Publication No. 2011/0301073.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; and 6,200,759 and International Patent Publication Nos. WO 95/19431; WO 96/06166; WO 98/53057; WO 98/54311; WO 00/27878; WO 01/60970; WO 01/88197; WO 02/099084; and U.S. Patent Publication No. 2011/0301073.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger or TALEN proteins can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or non-coding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miR-NAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 2007/0218528; 2008/0131962; and 2011/0201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "disease associated gene" is one that is defective in some manner in a monogenic disease. Non-limiting examples of monogenic diseases include severe combined immunodeficiency, cystic fibrosis, lysosomal storage diseases (e.g. Gaucher's, Hurler's Hunter's, Fabry's, Neimann-Pick, Tay-Sach's etc), sickle cell anemia, and thalassemia.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP or TALEN as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

"Red Blood Cells" (RBCs) or erythrocytes are terminally differentiated cells derived from hematopoietic stem cells. They lack a nucleus and most cellular organelles. RBCs contain hemoglobin to carry oxygen from the lungs to the peripheral tissues. In fact 33% of an individual RBC is hemoglobin. They also carry $CO_2$ produced by cells during metabolism out of the tissues and back to the lungs for release during exhale. RBCs are produced in the bone marrow in response to blood hypoxia which is mediated by release of erythropoietin (EPO) by the kidney. EPO causes an increase in the number of proerythroblasts and shortens the time required for full RBC maturation.

After approximately 120 days, since the RBC do not contain a nucleus or any other regenerative capabilities, the cells are removed from circulation by either the phagocytic activities of macrophages in the liver, spleen and lymph nodes (~90%) or by hemolysis in the plasma (~10%). Following macrophage engulfment, chemical components of the RBC are broken down within vacuoles of the macrophages due to the action of lysosomal enzymes.

"Secretory tissues" are those tissues in an animal that secrete products out of the individual cell into a lumen of some type which are typically derived from epithelium. Examples of secretory tissues that are localized to the gastrointestinal tract include the cells that line the gut, the pancreas, and the gallbladder. Other secretory tissues include the liver, tissues associated with the eye and mucous membranes such as salivary glands, mammary glands, the prostate gland, the pituitary gland and other members of the endocrine system. Additionally, secretory tissues include individual cells of a tissue type which are capable of secretion.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP or TALE DNA-binding domain is fused to an activation domain, the ZFP or TALE DNA-binding domain and the activation domain are in operative linkage if, in the fusion polypeptide, the ZFP or TALE DNA-binding domain portion is able to bind its target site and/or its binding site, while the activation domain is able to up-regulate gene expression. When a fusion polypeptide in which a ZFP or TALE DNA-binding domain is fused to a cleavage domain, the ZFP or TALE DNA-binding domain and the cleavage domain are in operative linkage if, in the fusion polypeptide, the ZFP or TALE DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields, et al., (1989) *Nature* 340:245-246; U.S. Pat. No. 5,585,245 and International Patent Publication No. WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the altered cells of the invention and/or proteins produced by the altered cells of the invention can be administered. Subjects of the present invention include those having an LSD.

Nucleases

Described herein are compositions, particularly nucleases, which are useful targeting a gene for the insertion of a transgene, for example, nucleases that are specific for a safe-harbor gene such as albumin. In certain embodiments, the nuclease is naturally occurring. In other embodiments, the nuclease is non-naturally occurring, i.e., engineered in the DNA-binding domain and/or cleavage domain. For example, the DNA-binding domain of a naturally-occurring nuclease or nuclease system may be altered to bind to a selected target site (e.g., a meganuclease that has been engineered to bind to site different than the cognate binding site or a CRISPR/Cas system utilizing an engineered single guide RNA). In other embodiments, the nuclease comprises heterologous DNA-binding and cleavage domains (e.g., zinc finger nucleases; TAL-effector nucleases; meganuclease DNA-binding domains with heterologous cleavage domains).

A. DNA-Binding Domains

In certain embodiments, the nuclease is a meganuclease (homing endonuclease). Naturally-occurring meganucleases recognize 15-40 base-pair cleavage sites and are commonly grouped into four families: the LAGLIDADG (SEQ ID NO: 133) family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort, et al., (1997) *Nucleic Acids Res*. 25:3379-3388; Dujon, et al., (1989) *Gene* 82:115-118; Perler, et al., (1994) Nucleic Acids Res. 22, 1125-1127; Jasin (1996) *Trends Genet*. 12:224-228; Gimble, et al., (1996) *J. Mol. Biol*. 263:163-180; Argast, et al., (1998) *J. Mol. Biol*. 280:345-353 and the New England Biolabs catalogue.

In certain embodiments, the nuclease comprises an engineered (non-naturally occurring) homing endonuclease (meganuclease). The recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort, et al., (1997) *Nucleic Acids Res*. 25:3379-3388; Dujon, et al., (1989) *Gene* 82:115-118; Perler, et al., (1994) Nucleic Acids Res. 22, 1125-1127; Jasin (1996) *Trends Genet*. 12:224228; Gimble, et al., (1996)*J. Mol. Biol*. 263:163-180; Argast, et al., (1998)*J. Mol. Biol*. 280:345-353 and the New England Biolabs catalogue. In addition, the DNA-binding specificity of homing endonucleases and meganucleases can be engineered to bind non-natural target sites. See, for example, Chevalier, et al., (2002) *Molec. Cell* 10:895-905; Epinat, et al., (2003) *Nucleic Acids Res*. 31:2952-2962; Ashworth, et al., (2006) *Nature* 441:656-659; Paques, et al., (2007) *Current Gene Therapy* 7:49-66; U.S. Patent Publication No. 2007/0117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain comprises a naturally occurring or engineered (non-naturally occurring) TAL effector DNA binding domain. See, e.g., U.S. Patent Publication No. 2011/0301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like effectors (TALE) which mimic plant transcriptional activators and manipulate the plant transcriptome (see Kay, et al., (2007) *Science* 318:648-651). These proteins contain a DNA binding domain and a transcriptional activation domain. One of the most well characterized TALEs is AvrBs3 from *Xanthomonas* campestgris pv. Vesicatoria (see Bonas, et al., (1989) Mol Gen Genet 218: 127-136 and International Patent Publication No. WO 2010/079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S., et al., (2006) J Plant Physiol 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer, et al., (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Thus, in some embodiments, the DNA binding domain that binds to a target site in a target locus (e.g., albumin or other safe harbor) is an engineered domain from a TAL effector similar to those derived from the plant pathogens *Xanthomonas* (see Boch, et al., (2009) *Science* 326: 1509-1512 and Moscou and Bogdanove, (2009) *Science* 326: 1501) and Ralstonia (see Heuer, et al., (2007) Applied and Environmental Microbiology 73(13): 4379-4384); U.S. Patent Publication Nos. 2011/0301073 and 2011/0145940. See, e.g., albumin TALENs in U.S. Pat. Nos. 9,394,545 and 9,150,847, incorporated by reference herein in their entireties.

In certain embodiments, the DNA binding domain comprises a zinc finger protein (e.g., a zinc finger protein that binds to a target site in an albumin or safe-harbor gene). Preferably, the zinc finger protein is non-naturally occurring in that it is engineered to bind to a target site of choice. See, for example, See, for example, Beerli, et al., (2002) *Nature Biotechnol.* 20:135-141; Pabo, et al., (2001) *Ann. Rev. Biochem.* 70:313-340; Isalan, et al., (2001) *Nature Biotechnol.* 19:656-660; Segal, et al., (2001) *Curr. Opin. Biotechnol.* 12:632-637; Choo, et al., (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding or TALE domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453, 242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as International Patent Publication Nos. WO 98/37186; WO 98/53057; WO 00/27878; WO 01/88197 and GB 2,338,237. In addition, enhancement of binding specificity for zinc finger binding domains has been described, for example, in co-owned International Patent Publication No. WO 02/077227.

In addition, as disclosed in these and other references, DNA domains (e.g., multi-fingered zinc finger proteins or TALE domains) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The DNA binding proteins described herein may include any combination of suitable linkers between the individual zinc fingers of the protein. In addition, enhancement of binding specificity for zinc finger binding domains has been described, for example, in co-owned International Patent Publication No. WO 02/077227.

Selection of target sites; DNA-binding domains and methods for design and construction of fusion proteins (and polynucleotides encoding same) are known to those of skill in the art and described in detail in U.S. Pat. Nos. 6,140, 0815; 789,538; 6,453,242; 6,534,261; 5,925,523; 6,007,988; 6,013,453; 6,200,759; International Patent Publication Nos. WO 95/19431; WO 96/06166; WO 98/53057; WO 98/54311; WO 00/27878; WO 01/60970; WO 01/88197; WO 02/099084; WO 98/53058; WO 98/53059; WO 98/53060; WO 02/016536; and WO 03/016496 and U.S. Patent Publication No. 2011/0301073.

In addition, as disclosed in these and other references, DNA-binding domains (e.g., multi-fingered zinc finger proteins) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim, et al., (1996) *Proc Nat'l Acad Sci USA* 93(3): 1156-1160. More recently, ZFNs have been used for genome modification in a variety of organisms. See, for example, U.S. Patent Publication Nos. 2003/0232410; 2005/0208489; 2005/0026157; 2005/0064474; 2006/0188987; 2006/0063231; and International Patent Publication No. WO 07/014275. Likewise, TALE DNA-binding domains have been fused to nuclease domains to create TALENs. See, e.g., U.S. Patent Publication No. 2011/0301073.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort, et al., (1997) *Nucleic Acids Res.* 25:3379-3388. Additional enzymes which cleave DNA are known (e.g., 51 Nuclease; mung bean nuclease; pancreatic DNase I; micrococcal nuclease; yeast HO endonuclease; see also Linn, et al., (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150; and 5,487,994; as well as Li, et al., (1992) *Proc. Natl. Acad. Sci. USA* 89:4275-4279; Li, et al., (1993) *Proc. Natl. Acad. Sci. USA* 90:2764-2768; Kim, et al., (1994a) *Proc. Natl. Acad. Sci. USA* 91:883-887; Kim, et al., (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite, et al., (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Patent Publication No. WO 07/014275, incorporated herein in its entirety. Additional restriction enzymes also contain separable binding and cleavage domains, and these are contemplated by the present disclosure. See, for example, Roberts, et al., (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 2005/0064474; 2006/0188987 and 2008/0131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes.

In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See U.S. Patent Publication No. 2011/0201055). Engineered cleavage half-domains described herein can be prepared using any suitable method, for example, by site-directed mutagenesis of wild-type cleavage half-domains (Fok I) as described in U.S. Patent Publication Nos. 2005/0064474; 2008/0131962; and 2011/0201055.

Alternatively, nucleases may be assembled in vivo at the nucleic acid target site using so-called "split-enzyme" technology (see e.g. U.S. Patent Publication No. 2009/0068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in International Patent Publication No. WO 2009/042163 and U.S. Patent Publication No. 2009/0068164. Nuclease expression constructs can be readily designed using methods known in the art. See, e.g., U.S. Patent Publication Nos. 2003/0232410; 2005/0208489; 2005/0026157; 2005/0064474; 2006/0188987; 2006/0063231; and International Patent Publication No. WO 07/014275. Expression of the nuclease may be under the control of a constitutive promoter or an inducible promoter, for example the galactokinase promoter which is activated (de-repressed) in the presence of raffinose and/or galactose and repressed in presence of glucose.

The CRISPR (Clustered Regularly Interspaced Short Palindromic Repeats)/Cas (CRISPR Associated) nuclease system is a recently engineered nuclease system based on a bacterial system that can be used for genome engineering. It is based on part of the adaptive immune response of many bacteria and archea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer". Cas9 cleaves the DNA to generate blunt ends at the DSB at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek, et al., (2012) *Science* 337, p. 816-821, Jinek, et al., (2013), *eLife* 2:e00471, and David Segal, (2013) *eLife* 2:e00563). Thus, the CRISPR/Cas system can be engineered to create a DSB at a desired target in a genome, and repair of the DSB can be influenced by the use of repair inhibitors to cause an increase in error prone repair.

Target Sites

As described in detail above, DNA domains can be engineered to bind to any sequence of choice in a locus, for example an albumin or other safe-harbor gene. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual (e.g., zinc finger) amino acid sequences, in which each triplet or quadruplet nucleotide sequence is associated with one or more amino acid sequences of DNA binding domain which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Patent Publication No. 2011/0301073.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as International Patent Publication Nos. WO 98/37186; WO 98/53057; WO 00/27878; WO 01/88197 and GB 2,338,237.

Selection of target sites; nucleases and methods for design and construction of fusion proteins (and polynucleotides encoding same) are known to those of skill in the art and described in detail in U.S. Patent Publication Nos. 2005/0064474 and 2006/0188987, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Patent Publication No. 2011/0301073.

Donors

As noted above, insertion of an exogenous sequence (also called a "donor sequence" or "donor"), for example for correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded or double-stranded and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang, et al., (1987) *Proc. Natl. Acad. Sci. USA* 84:4959-4963; Nehls, et al., (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is generally inserted so that its expression is driven by the endogenous promoter at the integration site, namely the promoter that drives expression of the endogenous gene into which the donor is inserted (e.g., highly expressed, albumin, AAVS1, HPRT, etc.). However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. For example, a transgene as described herein may be inserted into an albumin or other locus such that some (N-terminal and/or C-terminal to the transgene encoding the lysosomal enzyme) or none of the endogenous albumin sequences are expressed, for example as a fusion with the transgene encoding the lysosomal sequences. In other embodiments, the transgene (e.g., with or without additional coding sequences such as for albumin) is integrated into any endogenous locus, for example a safe-harbor locus. See, e.g., U.S. Patent Publication Nos. 2008/0299580; 2008/0159996 and 2010/00218264.

When endogenous sequences (endogenous or part of the transgene) are expressed with the transgene, the endogenous sequences (e.g., albumin, etc.) may be full-length sequences (wild-type or mutant) or partial sequences. Preferably the endogenous sequences are functional. Non-limiting examples of the function of these full length or partial sequences (e.g., albumin) include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

In certain embodiments, the exogenous sequence (donor) comprises a fusion of a protein of interest and, as its fusion partner, an extracellular domain of a membrane protein, causing the fusion protein to be located on the surface of the cell. This allows the protein encoded by the transgene to potentially act in the serum. In the case of treatment for an LSD, the enzyme encoded by the transgene fusion would be able to act on the metabolic products that are accumulating in the serum from its location on the surface of the cell (e.g., RBC). In addition, if the RBC is engulfed by a splenic macrophage as is the normal course of degradation, the lysosome formed when the macrophage engulfs the cell would expose the membrane bound fusion protein to the high concentrations of metabolic products in the lysosome at the pH more naturally favorable to that enzyme. Non-limiting examples of potential fusion partners are shown below in Table 1.

TABLE 1

Examples of potential fusion partners

| Name | Activity |
| --- | --- |
| Band 3 | Anion transporter, makes up to 25% of the RBC membrane surface protein |
| Aquaporin 1 | water transporter |
| Glut1 | glucose and L-dehydroascorbic acid transporter |
| Kidd antigen protein | urea transporter |
| RhAG | gas transporter |
| ATP1A1, ATP1B1 | Na+/K+—ATPase |
| ATP2B1, ATP2B2, ATP2B3, ATP2B4 | Ca2+—ATPase |
| NKCC1, NKCC2 | Na+ K+ 2Cl−—cotransporter |
| SLC12A3 | Na+—Cl−—cotransporter |
| SLC12A1, SLA12A2 | Na—K—cotransporter |
| KCC1 | K—Cl cotransporter |
| KCNN4 | Gardos Channel |

Lysosomal storage diseases typically fall into five classes. These classes are shown below in Table 2 along with specific examples of the diseases. Thus, the donor molecules described herein can include sequences coding for one or more enzymes lacking or deficient in subjects with lysosomal storage diseases, including but not limited to the proteins shown in Table 2.

TABLE 2

Lysosomal Storage Diseases

| Protein | Disease | Disease Associated Gene | Accumulated product |
| --- | --- | --- | --- |
| 1. DEFECTS IN GLYCAN DEGRADATION | | | |
| I. Defects in glycoprotein degradation | | | |
| α-Sialidase (neuraminidase) | Sialidosis | NEU1 | sialidated glycopeptides and oligosaccharides |
| Cathepsin A | Galactosialidosis | CTSA | polysaccharide |
| lysosomal alpha-mannosidase | α-Mannosidosis | MAN2B1 | mannose-rich glycoproteins and oligosaccharides |
| lysosomal beta-mannosidase | β-Mannosidosis | MANBA | |
| Glycosylasparaginase | Aspartylglucosaminuria | AGA | glycoasparagines |
| Alpha L Fucosidase | Fucosidosis | FUCA1 | fucose |
| α-N-Acetylglucosaminidase | Sanfilippo syndrome B | NAGLU | glycosaminoglycan |

TABLE 2-continued

Lysosomal Storage Diseases

| Protein | Disease | Disease Associated Gene | Accumulated product |
|---|---|---|---|
| II. Defects in glycolipid degradation <br> A. GM1 Ganglioside | | | |
| β-Galactosidase | GM1 gangliosidosis/MPS IVB | GLB1 | keratan sulfate |
| β-Hexosaminidase α-subunit | GM2-gangliosidosis (Tay-Sachs) | HEXA | GM2 ganglioside |
| β-Hexosaminidase β-subunit | GM2-gangliosidosis (Sandhoff) | HEXB | GM2 ganglioside |
| GM2 activator protein | GM2 gangliosidosis | GM2A | GM2 ganglioside |
| Glucocerebrosidase | Gaucher disease | GBA | glucocerebroside |
| Saposin C | Gaucher disease (atypical) | PSAP | glucocerebroside |
| B. Defects in the degradation of sulfatide | | | |
| Arylsulfatase A | Metachromatic leukodystrophy | ARSA | sulphatide |
| Saposin B | Metachromatic leukodystrophy | PSAP | sulphatide |
| Formyl-Glycin generating enzyme | Multiple sulfatase deficiency | SUMF1 | sulfated lipids |
| β-Galactosylceramidase (Krabbe) | Globoid cell leukodystrophy | GALC | galactocerebroside |
| C. Defects in degradation of globotriaosylceramide | | | |
| α-Galactosidase A | Fabry | GLA | globotriaosylceramide |
| III. Defects in degradation of Glycosaminoglycan (Mucopolysaccharidoses) <br> A. Degradation of heparan sulphate | | | |
| Iduronate sulfatase | MPS II (Hunter) | IDS | Dermatan sulfate, Heparan sulfate |
| Iduronidase | MPS 1 (Hurler, Scheie) | IDUA | Dermatan sulfate, Heparan sulfate |
| Heparan N-sulfatase | MPS IIIa (Sanfilippo A) | SGSH | Heparan sulfate |
| Acetyl-CoA transferase | MPS IIIc (Sanfilippo C) | HGSNAT | Heparan sulfate |
| N-acetyl glucosaminidase | MPS IIIb (Sanfilippo B) | NAGLU | Heparan sulfate |
| β-glucuronidase | MPS VII (Sly) | GUSB | |
| N-acetyl glucosamine 6-sulfatase | MPS IIId (Sanfilippo D) | GNS | Heparan sulfate |
| B. Degradation of other mucopolysaccharides | | | |
| B-Galactosidase | MPS VIB (Morquio B) | GLB1 | Keratan sulfate, |
| Galactose 6-sulfatase | MPS IVA (Morquio A) | GALNS | Keratan sulfate, Chondroitin 6-sulfate |
| Hyaluronidase | MPS IX | HYAL1 | Hyaluronic acid |
| C. Defects in degradation of glycogen | | | |
| α-Glucosidase | Pompe | GAA | Glycogen |
| 2. DEFECTS IN LIPID DEGRADATION <br> I. Defects in degradation of sphingomyelin | | | |
| Acid sphingomyelinase | Niemann Pick type A | SMPD1 | sphingomyelin |
| Acid ceramidase | Farber lipogranulomatosis | ASAH1 | nonsulfonated acid mucopolysaccharide |
| II. Defects in degradation of triglycerides and cholesteryls ester | | | |
| Acid lipase | Wolman and cholesteryl ester storage disease | LIPA | cholesteryl esters |
| 3. DEFECTS IN PROTEIN DEGRADATION | | | |
| Cathepsin K | Pycnodystostosis | CTSK | |
| Tripeptidyl peptidase | Ceroide lipofuscinosis | PPT2 | |
| Palmitoyl-protein thioesterase | Ceroide lipofuscinosis | PPT1 | |
| 4. DEFECTS IN LYSOSOMAL TRANSPORTERS | | | |
| Cystinosin (cystin transport) | Cystinosis | CTNS | |
| Sialin (sialic acid transport) | Salla disease | SLC17A5 | N-acetylneuraminic acid |
| 5. DEFECTS IN LYSOSOMAL TRAFFICKING PROTEINS | | | |
| Phosphotransferase γ-subunit | Mucolipidosis III (I-cell) | GNPTG | |
| Mucolipin-1 (cation channel) | Mucolipidosis | MCOLN1 | |
| LYSOSOME-ASSOCIATED MEMBRANE PROTEIN 2 | Danon | LAMP2 | |
| Niemann-Pick disease, type C1 | Niemann Pick type C | NPC1 | LDL cholesterol |

TABLE 2-continued

Lysosomal Storage Diseases

| Protein | Disease | Disease Associated Gene | Accumulated product |
|---|---|---|---|
| palmitoyl-protein thioesterase-1 | Ceroid lipofuscinosis (Batten Disease) | CLN3 | autofluorescent lipopigment storage material |
| neuronal ceroid lipofuscinosis-6 | Ceroid lipofuscinosis 6 | CLN 6 | |
| neuronal ceroid lipofuscinosis-8 | Ceroid lipofuscinosis 8 | CLN 8 | |
| LYSOSOMAL TRAFFICKING REGULATOR | Chediak-Higashi | LYST | |
| Myocilin | Griscelli Type 1 | MYOC | |
| RAS-associated protein 27A | Griscelli Type 2 | RAB27A | |
| Melanophilin | Griscelli Type 3 | MLPH or MYO5A | |
| AP3 β-subunit | Hermansky Pudliak | AP3B1 | ceroid |

In some cases, the donor may be an endogenous gene that has been modified. Although antibody response to enzyme replacement therapy varies with respect to the specific therapeutic enzyme in question and with the individual patient, a significant immune response has been seen in many LSD patients being treated with enzyme replacement. In addition, the relevance of these antibodies to the efficacy of treatment is also variable (see Katherine Ponder, (2008) *J Clin Invest* 118(8):2686). Thus, the methods and compositions of the current invention can comprise the use of donor molecules whose sequence has been altered by functionally silent amino acid changes at sites known to be priming epitopes for endogenous immune responses, such that the polypeptide produced by such a donor is less immunogenic.

LSD patients often have neurological sequelae due the lack of the missing enzyme in the brain. Unfortunately, it is often difficult to deliver therapeutics to the brain via the blood due to the impermeability of the blood brain barrier. Thus, the methods and compositions of the invention may be used in conjunction with methods to increase the delivery of the therapeutic into the brain. There are some methods that cause a transient opening of the tight junctions between cells of the brain capillaries. Examples include transient osmotic disruption through the use of an intracarotid administration of a hypertonic mannitol solution, the use of focused ultrasound and the administration of a bradykinin analogue. Alternatively, therapeutics can be designed to utilize receptors or transport mechanisms for specific transport into the brain. Examples of specific receptors that may be used include the transferrin receptor, the insulin receptor or the low-density lipoprotein receptor related proteins 1 and 2 (LRP-1 and LRP-2). LRP is known to interact with a range of secreted proteins such as apoE, tPA, PAI-1 etc, and so fusing a recognition sequence from one of these proteins for LRP may facilitate transport of the enzyme into the brain, following expression in the liver of the therapeutic protein and secretion into the blood stream (see Gabathuler, (2010) ibid).

Delivery

The nucleases, polynucleotides encoding these nucleases, donor polynucleotides and compositions comprising the proteins and/or polynucleotides described herein may be delivered in vivo or ex vivo by any suitable means.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the zinc finger or TALEN protein(s). Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada, et al., in *Current Topics in Microbiology and Immunology* Doerfler and Bohm (eds.) (1995); and Yu, et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, International Patent Publication Nos. WO 91/17424, WO 91/16024.

The preparation of lipid:nucleic acid complexes, including targeted liposomes such as immunolipid complexes, is well known to one of skill in the art (see, e.g., Crystal, Science 270:404-410 (1995); Blaese, et al., Cancer Gene Ther. 2:291-297 (1995); Behr, et al., Bioconjugate Chem. 5:382-389 (1994); Remy, et al., Bioconjugate Chem. 5:647-654 (1994); Gao, et al., Gene Therapy 2:710-722 (1995); Ahmad, et al., Cancer Res. 52:4817-4820 (1992); U.S. Pat. Nos. 4,186,183; 4,217,344; 4,235,871; 4,261,975; 4,485,054; 4,501,728; 4,774,085; 4,837,028; and 4,946,787).

Additional methods of delivery include the use of packaging the nucleic acids to be delivered into EnGenelC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid, et al., (2009) Nature Biotechnology 27(7):643).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher, et al., J. Virol. 66:2731-2739 (1992); Johann, et al., J. Virol. 66:1635-1640 (1992); Sommerfelt, et al., Virol. 176:58-59 (1990); Wilson, et al., J. Virol. 63:2374-2378 (1989); Miller, et al., J. Virol. 65:2220-2224 (1991); International Patent Publication No. WO 1994/026877).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West, et al., Virology 160:38-47 (1987); U.S. Pat. No. 4,797,368; International Patent Publication No. WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin, et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski, et al., J. Virol. 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar, et al., Blood 85:3048-305 (1995); Kohn, et al., Nat. Med. 1:1017-102 (1995); Malech, et al., PNAS 94:22 12133-12138 (1997)). PA317/pLASN was the first therapeutic vector used in a gene therapy trial. (Blaese, et al., Science 270:475-480 (1995)). Transduction efficiencies of 50% or greater have been observed for MFG-S packaged vectors. (Ellem, et al., Immunol Immunother. 44(1):10-20 (1997); Dranoff, et al., Hum. Gene Ther. 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner, et al., Lancet 351:9117 1702-3 (1998), Kearns, et al., Gene Ther. 9:748-55 (1996)). Other AAV serotypes, including by non-limiting example, AAV1, AAV3, AAV4, AAV5, AAV6, AAV8, AAV 8.2, AAV9, and AAV rh10 and pseudotyped AAV such as AAV2/8, AAV2/5 and AAV2/6 can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman, et al., Hum. Gene Ther. 7:1083-9 (1998)). Additional examples of the use of adenovirus vectors for gene transfer in clinical trials include Rosenecker, et al., *Infection* 24:1 5-10 (1996); Sterman, et al., *Hum. Gene Ther.* 9:7 1083-1089 (1998); Welsh, et al., *Hum. Gene Ther.* 2:205-18 (1995); Alvarez, et al., *Hum. Gene Ther.* 5:597-613 (1997); Topf, et al., *Gene Ther.* 5:507-513 (1998); Sterman, et al., *Hum. Gene Ther.* 7:1083-1089 (1998).

Packaging cells are used to form virus particles that are capable of infecting a host cell. Such cells include 293 cells, which package adenovirus, and w2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han, et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors (IDLV). See, for example, Ory, et al. (1996) *Proc. Natl. Acad. Sci. USA* 93:11382-11388; Dull, et al. (1998) *J. Virol.* 72:8463-8471; Zuffery, et al., (1998) *J. Virol.* 72:9873-9880; Follenzi, et al., (2000) *Nature Genetics* 25:217-222; U.S. Patent Publication No. 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

It will be apparent that the nuclease-encoding sequences and donor constructs can be delivered using the same or different systems. For example, a donor polynucleotide can be carried by a plasmid, while the one or more nucleases can be carried by a AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Applications

The methods of this invention contemplate the treatment of a monogenic disease (e.g. lysosomal storage disease). Treatment can comprise insertion of the corrected disease associated gene in safe harbor locus (e.g. albumin) for expression of the needed enzyme and release into the blood stream. Insertion into a secretory cell, such as a liver cell for release of the product into the blood stream, is particularly useful. The methods and compositions of the invention also can be used in any circumstance wherein it is desired to supply a transgene encoding one or more therapeutics in a hemopoietic stem cell such that mature cells (e.g., RBCs) derived from these cells contain the therapeutic. These stem cells can be differentiated in vitro or in vivo and may be derived from a universal donor type of cell which can be used for all patients. Additionally, the cells may contain a transmembrane protein to traffic the cells in the body. Treatment can also comprise use of patient cells containing the therapeutic transgene where the cells are developed ex vivo and then introduced back into the patient. For example, HSC containing a suitable transgene may be inserted into a patient via a bone marrow transplant. Alternatively, stem cells such as muscle stem cells or iPSC which have been edited using with the therapeutic transgene maybe also injected into muscle tissue.

Thus, this technology may be of use in a condition where a patient is deficient in some protein due to problems (e.g., problems in expression level or problems with the protein expressed as sub- or non-functioning). Particularly useful with this invention is the expression of transgenes to correct or restore functionality in lysosomal storage disorders.

By way of non-limiting examples, production of the defective or missing proteins accomplished and used to treat the lysosomal storage disease. Nucleic acid donors encoding the proteins may be inserted into a safe harbor locus (e.g. albumin or HPRT) and expressed either using an exogenous promoter or using the promoter present at the safe harbor. Alternatively, donors can be used to correct the defective gene in situ. The desired transgene may be inserted into a CD34+ stem cell and returned to a patient during a bone marrow transplant. Finally, the nucleic acid donor maybe be inserted into a CD34+ stem cell at a beta globin locus such that the mature red blood cell derived from this cell has a high concentration of the biologic encoded by the nucleic acid donor. The biologic containing RBC can then be targeted to the correct tissue via transmembrane proteins (e.g. receptor or antibody). Additionally, the RBCs may be sensitized ex vivo via electrosensitization to make them more susceptible to disruption following exposure to an energy source (see International Patent Publication No. WO 2002/007752).

In some applications, an endogenous gene may be knocked out by use of the methods and compositions of the invention. Examples of this aspect include knocking out an aberrant gene regulator or an aberrant disease associated gene. In some applications, an aberrant endogenous gene may be replaced, either functionally or in situ, with a wild type version of the gene. The inserted gene may also be altered to improve the functionality of the expressed protein or to reduce its immunogenicity. In some applications, the inserted gene is a fusion protein to increase its transport into a selected tissue such as the brain.

The following Examples relate to exemplary embodiments of the present disclosure in which the nuclease comprises a zinc finger nuclease (ZFN) or TALEN. It will be appreciated that this is for purposes of exemplification only and that other nucleases or nuclease systems can be used, for instance homing endonucleases (meganucleases) with engineered DNA-binding domains and/or fusions of naturally occurring of engineered homing endonucleases (meganucleases) DNA-binding domains and heterologous cleavage domains and/or a CRISPR/Cas system comprising an engineered single guide RNA.

EXAMPLES

Example 1

Design, Construction and General Characterization of Albumin-specific Nucleases

Zinc finger proteins were designed and incorporated into plasmids, AAV or adenoviral vectors essentially as described in Urnov, et al., (2005) *Nature* 435(7042):646-651, Perez, et al., (2008) *Nature Biotechnology* 26(7):808-816, and as described in U.S. Pat. No. 6,534,261. Table 3 shows the recognition helices within the DNA binding domain of exemplary albumin-specific ZFPs while Table 4 shows the target sites for these ZFPs (see co-owned U.S. Provisional Patent Application Nos. 61/537,349 and 61/560,506). Nucleotides in the target site that are contacted by the ZFP recognition helices are indicated in uppercase letters; non-contacted nucleotides indicated in lowercase. Albumin-specific TALENs were also designed and are set forth in U.S. Pat. Nos. 9,394,545 and 9,150,847 and incorporated by reference in their entireties.

TABLE 3

Murine albumin-specific zinc finger nucleases helix designs

| Target SBS # | Design | | | | | |
|---|---|---|---|---|---|---|
| | F1 | F2 | F3 | F4 | F5 | F6 |
| Intron 30724 1 | TSGSLTR (SEQ ID NO: 1) | RSDALST (SEQ ID NO: 2) | QSATRTK (SEQ ID NO: 3) | TSGHLSR (SEQ ID NO: 4) | QSGNLAR (SEQ ID NO: 5) | NA |
| Intron 30725 1 | RSDHLSA (SEQ ID NO: 6) | TKSNRTK (SEQ ID NO: 7) | DRSNLSR (SEQ ID NO: 8) | WRSSLRA (SEQ ID NO: 9) | DSSDRKK (SEQ ID NO: 10) | NA |
| Intron 30732 1 | TSGNLTR (SEQ ID NO: 11) | DRSTRRQ (SEQ ID NO: 12) | TSGSLTR (SEQ ID NO: 1) | ERGTLAR (SEQ ID NO: 13) | TSANLSR (SEQ ID NO: 14) | NA |
| Intron 30733 1 | DRSALAR (SEQ ID NO: 15) | RSDHLSE (SEQ ID NO: 16) | HRSDRTR (SEQ ID NO: 17) | QSGALAR (SEQ ID NO: 18) | QSGHLSR (SEQ ID NO: 19) | NS |
| Intron 30759 13 | RSDNLST (SEQ ID NO: 20) | DRSALAR (SEQ ID NO: 15) | DRSNLSR (SEQ ID NO: 8) | DGRNLRH (SEQ ID NO: 21) | RSDNLAR (SEQ ID NO: 22) | QSNALNR (SEQ ID NO: 23) |
| Intron 30761 13 | DRSNLSR (SEQ ID NO: 8) | LKQVLVR (SEQ ID NO: 24) | QSGNLAR (SEQ ID NO: 5) | QSTPLFA (SEQ ID NO: 25) | QSGALAR (SEQ ID NO: 18) | NA |
| Intron 30760 13 | DRSNLSR (SEQ ID NO: 8) | DGRNLRH (SEQ ID NO: 21) | RSDNLAR (SEQ ID NO: 22) | QSNALNR (SEQ ID NO: 23) | NA | NA |

TABLE 3-continued

Murine albumin-specific zinc finger nucleases helix designs

| Target | SBS # | F1 | F2 | F3 | F4 | F5 | F6 |
|---|---|---|---|---|---|---|---|
| Intron 13 | 30767 | RSDNLSV (SEQ ID NO: 26) | HSNARKT (SEQ ID NO: 27) | RSDSLSA (SEQ ID NO: 28) | QSGNLAR (SEQ ID NO: 5) | RSDSLSV (SEQ ID NO: 29) | QSGHLSR (SEQ ID NO: 19) |
| Intron 13 | 30768 | RSDNLSE (SEQ ID NO: 30) | ERANRNS (SEQ ID NO: 31) | QSANRTK (SEQ ID NO: 32) | ERGTLAR (SEQ ID NO: 13) | RSDALTQ (SEQ ID NO: 33) | NA |
| Intron 13 | 30769 | TSGSLTR (SEQ ID NO: 1) | DRSNLSR (SEQ ID NO: 8) | DGRNLRH (SEQ ID NO: 21) | ERGTLAR (SEQ ID NO: 13) | RSDALTQ (SEQ ID NO: 33) | NA |
| Intron 12 | 30872 | QSGHLAR (SEQ ID NO: 34) | RSDHLTQ (SEQ ID NO: 35) | RSDHLSQ (SEQ ID NO: 36) | WRSSLVA (SEQ ID NO: 37) | RSDVLSE (SEQ ID NO: 38) | RNQHRKT (SEQ ID NO: 39) |
| Intron 12 | 30873 | QSGDLTR (SEQ ID NO: 40) | RSDALAR (SEQ ID NO: 41) | QSGDLTR (SEQ ID NO: 40) | RRDPLIN (SEQ ID NO: 42) | RSDNLSV (SEQ ID NO: 26) | IRSTLRD (SEQ ID NO: 43) |
| Intron 12 | 30876 | RSDNLSV (SEQ ID NO: 26) | YSSTRNS (SEQ ID NO: 44) | RSDHLSA (SEQ ID NO: 6) | SYWSRTV (SEQ ID NO: 45) | QSSDLSR (SEQ ID NO: 46) | RTDALRG (SEQ ID NO: 47) |
| Intron 12 | 30877 | RSDNLST (SEQ ID NO: 20) | QKSPLNT (SEQ ID NO: 48) | TSGNLTR (SEQ ID NO: 11) | QAENLKS (SEQ ID NO: 49) | QSSDLSR (SEQ ID NO: 46) | RTDALRG (SEQ ID NO: 47) |
| Intron 12 | 30882 | RSDNLSV (SEQ ID NO: 26) | RRAHLNQ (SEQ ID NO: 50) | TSGNLTR (SEQ ID NO: 11) | SDTNRFK (SEQ ID NO: 51) | RSDNLST (SEQ ID NO: 20) | QSGHLSR (SEQ ID NO: 19) |
| Intron 12 | 30883 | DSSDRKK (SEQ ID NO: 10) | DRSALSR (SEQ ID NO: 52) | TSSNRKT (SEQ ID NO: 53) | QSGALAR (SEQ ID NO: 18) | RSDHLSR (SEQ ID NO: 54) | NA |

TABLE 4

Target sites of murine albumin-specific ZFNs

| Target | SBS # | Target site |
|---|---|---|
| Intron 1 | 30724 | ctGAAGGTgGCAATGGTTcctctctgct_ (SEQ ID NO: 55) |
| Intron 1 | 30725 | ttTCCTGTAACGATCGGgaactggcatc_ (SEQ ID NO: 56) |
| Intron 1 | 30732 | aaGATGCCaGTTCCCGATCgttacagga_ (SEQ ID NO: 57) |
| Intron 1 | 30733 | agGGAGTAGCTTAGGTCagtgaagagaa_ (SEQ ID NO: 58) |
| Intron 13 | 30759 | acGTAGAGAACAACATCTAGattggtgg_ (SEQ ID NO: 59) |
| Intron 13 | 30761 | ctGTAATAGAAACTGACttacgtagctt_ (SEQ ID NO: 60) |
| Intron 13 | 30760 | acGTAGAGAACAACatctagattggtgg_ (SEQ ID NO: 59) |
| Intron 13 | 30767 | agGGAATGtGAAATGATTCAGatatata_ (SEQ ID NO: 61) |
| Intron 13 | 30768 | ccATGGCCTAACAACAGtttatcttctt_ (SEQ ID NO: 62) |
| Intron 13 | 30769 | ccATGGCCtAACAACaGTTtatcttctt_ (SEQ ID NO: 62) |
| Intron 12 | 30872 | ctTGGCTGTGTAGGAGGGGAgtagcagt_ (SEQ ID NO: 63) |
| Intron 12 | 30873 | ttCCTAAGTTGGCAGTGGCAtgcttaat_ (SEQ ID NO: 64) |
| Intron 12 | 30876 | ctTTGGCTTTGAGGATTAAGcatgccac_ (SEQ ID NO: 65) |
| Intron 12 | 30877 | acTTGGCTcCAAGATTTATAGccttaaa_ (SEQ ID NO: 66) |
| Intron 12 | 30882 | caGGAAAGTAAGATAGGAAGgaatgtga_ (SEQ ID NO: 67) |
| Intron 12 | 30883 | ctGGGGTAAATGTCTCCttgctcttctt_ (SEQ ID NO: 68) |

Example 2

Activity of Murine Albumin-specific Nucleases

ZFN pairs targeting the murine albumin gene were used to test the ability of these ZFNs to induce DSBs at a specific target site. The amino acid sequence of the recognition helix region of the indicated ZFNs are shown below in Table 3 and their target sites shown in Table 4 (DNA target sites indicated in uppercase letters; non-contacted nucleotides indicated in lowercase).

The Cel-I assay (Surveyor™, Transgenomics) as described in Perez, et al., (2008) *Nat. Biotechnol.* 26: 808-816 and Guschin, et al., (2010) *Methods Mol Biol.* 649:247-56), was used to detect ZFN-induced modifications. In this assay, PCR-amplification of the target site was followed by quantification of insertions and deletions (indels) using the mismatch detecting enzyme Cel-I (Yang, et al., (2000) *Biochemistry* 39, 3533-3541) which provided a lower-limit estimate of DSB frequency. Three days following transfection of the ZFN expression vector at either standard conditions (37° C.) or using a hypothermic shock (30° C., see co-owned U.S. Patent Publication No. 2011/0041195), genomic DNA was isolated from Neuro2A cells transfected with the ZFN(s) using the DNeasy™ kit (Qiagen). In these experiments, all ZFN pairs were ELD/KKR FokI mutation pairs (described above).

A composite of the results from the Cel-I assay are shown in FIGS. 1A and 1B, and demonstrate that the ZFNs shown below are capable of inducing cleavage at their respective target sites. The percent indels shown beneath the lanes indicates the amount of genomes that were altered by NHEJ following cleavage. The data also demonstrates increased activity when the transduction procedure incorporates the hypothermic shock.

Example 3

In Vivo Cleavage of the Albumin Locus

The mouse albumin specific ZFNs SBS30724 and SBS30725 which target a sequence in intron 1 were tested in vivo. The ZFNs were introduced into an AAV2/8 vector as described previously (Li, et al., (2011) *Nature* 475 (7355): 217). To facilitate production in the baculovirus system, the vector AAV2/8.2 was used for preparations destined for baculoviral production. AAV2/8.2 differs from the AAV2/8 vector in that a portion of the AAV8 capsid has been removed and replaced by a same region from the AAV2 capsid creating a chimeric capsid. The region is the phospholipase A2 domain in VP1. Production of the ZFN containing virus particles was done either by preparation using a HEK293 system or a baculovirus system using standard methods in the art (See Li, et al., ibid, see e.g. U.S. Pat. No. 6,723,551). The virus particles were then administered to normal male mice (n=6) using a single dose of 200 microliter of 1.0e11 total vector genomes of either AAV2/8 or AAV2/8.2 encoding the mouse albumin-specific ZFN. 14 days post administration of rAAV vectors, mice were sacrificed, livers harvested and processed for DNA or total proteins using standard methods known in the art. Detection of AAV vector genome copies was performed by quantitative PCR. Briefly, qPCR primers were made specific to the bGHpA sequences within the AAV as follows:

```
                               (SEQ ID NO: 69)
Oligo200 (Forward)   5'-GTTGCCAGCCATCTGTTGTTT-3'

(SEQ ID NO: 70)
Oligo201 (Reverse)   5'-GACAGTGGGAGTGGCACCTT-3'

(SEQ ID NO: 71)
Oligo202 (Probe)     5'-CTCCCCCGTGCCTTCCTTGACC-3'
```

Figures 3A, 3B:
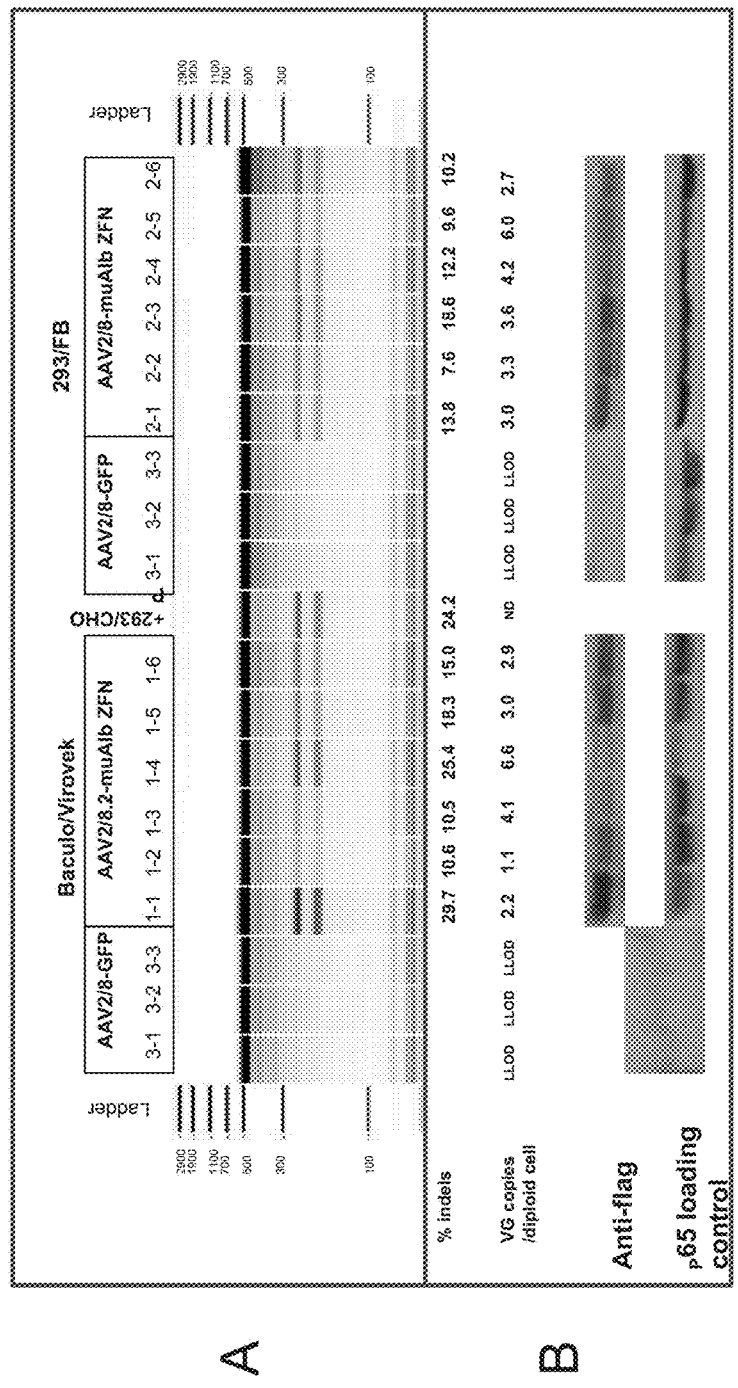
FIGS. 3A and 3B demonstrate activity of the mouse albumin ZFNs in vivo. Normal male mice (n=6) were administered a single dose of 200 microliter of $1.0 \times 10^{11}$ total vector genomes of either AAV2/8 or AAV2/8.2 encoding the murine specific ZFN pair SBS30724 and SBS30725 to evaluate liver infectivity by detection of AAV vector genome copies and in vivo NHEJ activity in normal mice. Vectors were given by tail vein injection into mice as described, and 14 days post administration, mice were sacrificed, livers harvested and processed for DNA or total protein quantification. Detection of AAV vector genome copies was performed by quantitative PCR and cleavage activity of the ZFN was measured using the Cel-1 (Surveyor, Transkaryotic) assay.

Cleavage activity of the ZFN was measured using a Cel-1 assay performed using a LC-GX apparatus (Perkin Elmer), according to manufacturer's protocol. Expression of the ZFNs in vivo was measured using a FLAG-Tag system according to standard methods. The results (FIGS. 3A and 3B) demonstrated that the ZFNs were expressed, and that they are active in cleaving the target in the mouse liver gene. Shown in the Figures are the Cel-I NHEJ results for each mouse in the study. The type of vector and their contents are shown above the lanes. Mismatch repair following ZFN cleavage (indicated % indels) was detected at nearly 16% in some of the mice.

Albumin-specific TALENs were also tested as set forth in U.S. Pat. Nos. 9,394,545 and 9,150,847 and incorporated by reference in their entireties).

Example 4

In Vivo Insertion of a Corrected Disease Associated Gene

The murine specific albumin ZFNs or TALENs are then used to introduce transgene encoding a therapeutic gene product into the albumin locus for expression. Donors were designed to insert the correct gene for Fabry's disease (GLA), Gaucher's disease (GBA), Hurler's disease (IDUA), and Hunter's disease into the albumin locus. In these donor constructs, the therapeutic gene was flanked by sequences homologous to the albumin gene. 5' of the transgene, the donor constructs all contain sequences homologous to the murine albumin intron 1, while 3' of the gene, the constructs contain sequences homologous to the murine albumin intron 1-exon 2 boundary.

The donor constructs are then incorporated into an AAV genome and the resulting AAV particles containing the donors are then purified using methods know in the art. The material is used to produce AAV viruses containing AAV-donor genomes using the triple transfection method into HEK 293T cells and purified on CsCl density gradients as has been described (see Ayuso, et al., (2010) *Gene Ther* 17(4), 503-510). AAV vector will be diluted in PBS prior to injection. A range of 5e9 to 5e13 v.g. AAV-donor vector particles will be used in conjunction with 1e9 to 1e12 vg of AAV-ZFN vector particles via tail vein or intraperitoneal injections of the viruses in wild-type, or disease model mice. AAV-ZFN genomes, described previously, containing the mouse albumin-specific ZFNs will be used, in combination with the GLA, GBA, IDUA and IDS AAV-donors. Cel-I and PCR assays will be performed on liver DNA isolated at various time points to determine the frequency of NHEJ and ZFN induced donor insertion. Southern blots may also be used. As per standard protocol, quantification of human GLA, GBA, IDUA and IDS in plasma will be performed using a human GLA, GBA, IDUA and IDS ELISA kit or using a FLAG Tag ELISA kit. Standard Western blots are also performed. The results demonstrate that these corrective transgenes can increase the expression of the therapeutic protein in vivo.

Figures 4A, 4B:
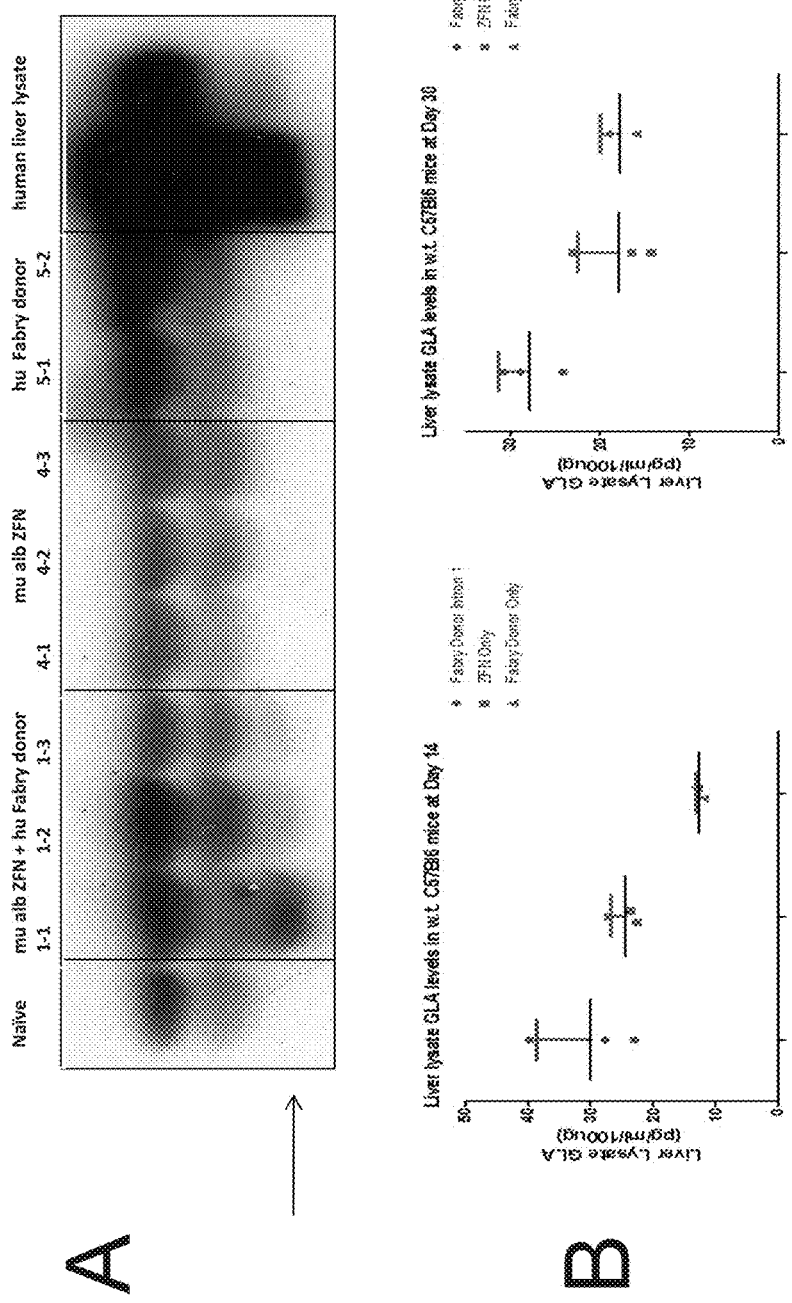
FIGS. 4A and 4B demonstrate the insertion of a huGLa transgene donor (deficient in patients afflicted with Fabry's disease) into the albumin locus in mice.
Figures 5A, 5B, 5C, 5D:
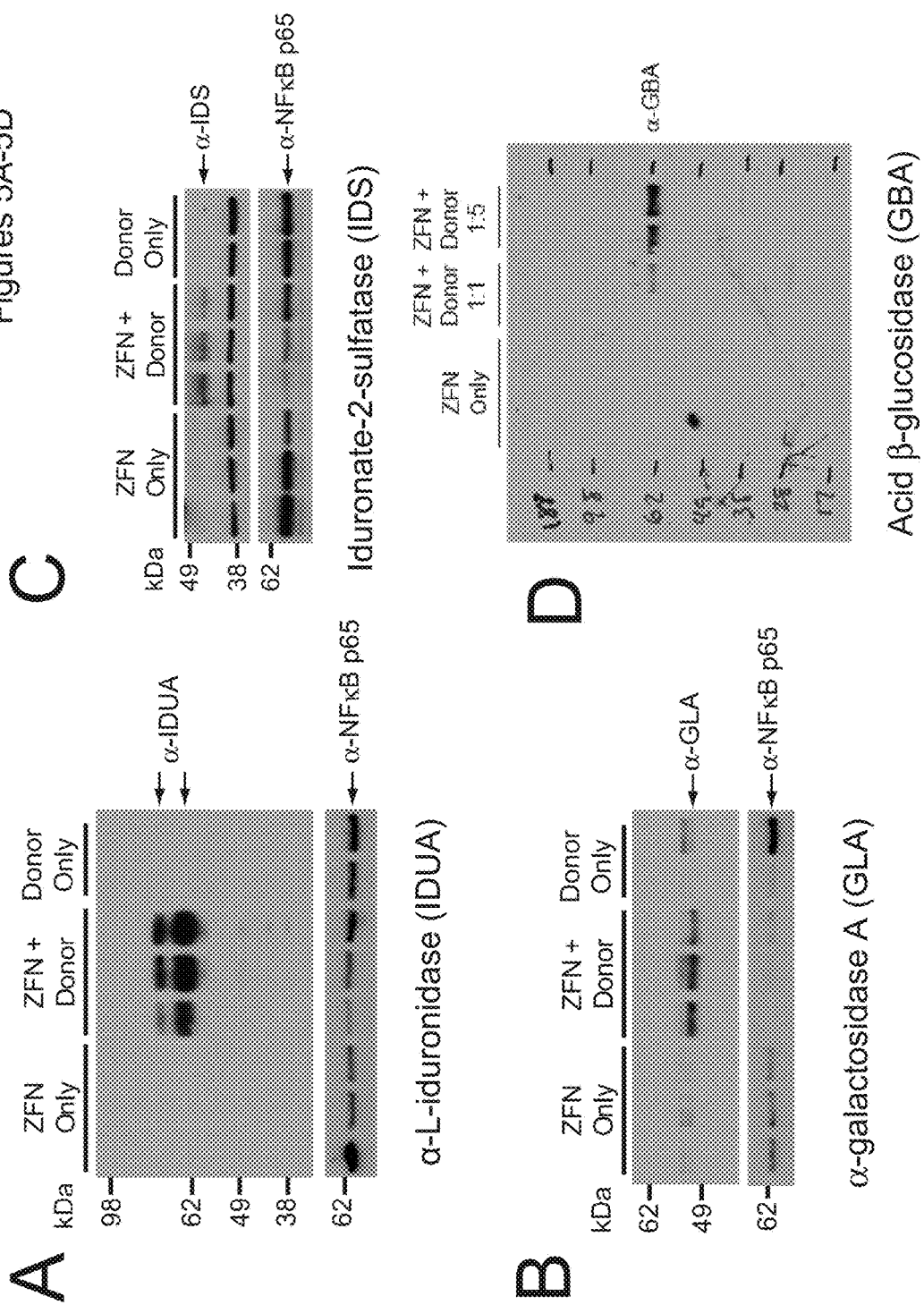
FIGS. 5A through 5D depicts Western blots that demonstrate expression in liver homogenates of the LSD donor transgenes inserted into the albumin locus in mice.

For example, the gene encoding human alpha galatosidase (deficient in patients with Fabry's disease) was inserted into the mouse albumin locus. The ZFN pair 30724/30725 was used as described above using a alpha galactosidase transgene. In this experiment, 3 mice were treated with an AAV2/8 virus containing the ZFN pair at a dose of 3.0e11 viral genomes per mouse and an AAV2/8 virus containing the huGLa donor at 1.5e12 viral genomes per mouse. Control animals were given either the ZFN containing virus alone or the huGLa donor virus alone. Western blots done on liver homogenates showed an increase in alpha galactosidase-specific signal, indicating that the alpha galactosidase gene had been integrated and was being expressed (FIG. 4A). In addition, an ELISA was performed on the liver lysate using a human alpha galactosidase assay kit (Sino) according to manufacturer's protocol. The results, shown in FIG. 4B, demonstrated an increase in signal in the mice that had been treated with both the ZFNs and the huGLa donor.

Example 5

Design of Human Albumin Specific ZFNs

To design ZFNs with specificity for the human albumin gene, the DNA sequence of human albumin intron 1 was analyzed using previously described methods to identify target sequences with the best potential for ZFN binding (for details, see co-owned U.S. Pat. Nos. 9,394,545 and 9,150,847). The target and helices are shown in Tables 5 and 6.

TABLE 5

Human albumin-specific zinc finger nucleases helix designs

| Target | SBS # | F1 | F2 | F3 | F4 | F5 | F6 |
|---|---|---|---|---|---|---|---|
| Intron 1 | 35393 | QSSDLSR (SEQ ID NO: 46) | LRHNLRA (SEQ ID NO: 72) | DQSNLRA (SEQ ID NO: 73) | RPYTLRL (SEQ ID NO: 74) | QSSDLSR (SEQ ID NO: 46) | HRSNLNK (SEQ ID NO: 75) |
| Intron 1 | 35394 | QSSDLSR (SEQ ID NO: 46) | HRSNLNK (SEQ ID NO: 75) | DQSNLRA (SEQ ID NO: 73) | RPYTLRL (SEQ ID NO: 74) | QSSDLSR (SEQ ID NO: 46) | HRSNLNK (SEQ ID NO: 75) |
| Intron 1 | 35396 | QSSDLSR (SEQ ID NO: 46) | LKWNLRT (SEQ ID NO: 76) | DQSNLRA (SEQ ID NO: 73) | RPYTLRL (SEQ ID NO: 74) | QSSDLSR (SEQ ID NO: 46) | HRSNLNK (SEQ ID NO: 75) |
| Intron 1 | 35398 | QSSDLSR (SEQ ID NO: 46) | LRHNLRA (SEQ ID NO: 72) | DQSNLRA (SEQ ID NO: 73) | RPYTLRL (SEQ ID NO: 74) | QSSDLSR (SEQ ID NO: 46) | HRSNLNK (SEQ ID NO: 75) |
| Intron 1 | 35399 | QSSDLSR (SEQ ID NO: 46) | HRSNLNK (SEQ ID NO: 75) | DQSNLRA (SEQ ID NO: 73) | RPYTLRL (SEQ ID NO: 74) | QSSDLSR (SEQ ID NO: 46) | HRSNLNK (SEQ ID NO: 75) |
| Intron 1 | 35405 | QSSDLSR (SEQ ID NO: 46) | WKWNLRA (SEQ ID NO: 77) | DQSNLRA (SEQ ID NO: 73) | RPYTLRL (SEQ ID NO: 74) | QSSDLSR (SEQ ID NO: 46) | HRSNLNK (SEQ ID NO: 75) |
| Intron 1 | 35361 | QSGNLAR (SEQ ID NO: 5) | LMQNRNQ (SEQ ID NO: 78) | LKQHLNE (SEQ ID NO: 79) | TSGNLTR (SEQ ID NO: 11) | RRYYLRL (SEQ ID NO: 80) | N/A |
| Intron 1 | 35364 | QSGNLAR (SEQ ID NO: 5) | HLGNLKT (SEQ ID NO: 81) | LKQHLNE (SEQ ID NO: 79) | TSGNLTR (SEQ ID NO: 11) | RRDWRRD (SEQ ID NO: 82) | N/A |
| Intron 1 | 35370 | QSGNLAR (SEQ ID NO: 5) | LMQNRNQ (SEQ ID NO: 78) | LKQHLNE (SEQ ID NO: 79) | TSGNLTR (SEQ ID NO: 11) | RRDWRRD (SEQ ID NO: 82) | N/A |
| Intron 1 | 35379 | QRSNLVR (SEQ ID NO: (83) | TSSNRKT (SEQ ID NO: 53) | LKHHLTD (SEQ ID NO: 84) | TSGNLTR (SEQ ID NO: 11) | RRDWRRD (SEQ ID NO: 82) | N/A |
| Intron 1 | 35458 | DKSYLRP (SEQ ID NO: 85) | TSGNLTR (SEQ ID NO: 11) | HRSARKR (SEQ ID NO: 86) | QSSDLSR (SEQ ID NO: 46) | WRSSLKT (SEQ ID NO: 87) | N/A |
| Intron 1 | 35480 | TSGNLTR (SEQ ID NO: 11) | HRSARKR (SEQ ID NO: 86) | QSGDLTR (SEQ ID NO: 40) | NRHHLKS (SEQ ID NO: 88) | N/A | N/A |
| Intron 1 | 35426 | QSGDLTR (SEQ ID NO: 40) | QSGNLHV (SEQ ID NO: 89) | QSAHRKN (SEQ ID NO: 90) | STAALSY (SEQ ID NO: 91) | TSGSLSR (SEQ ID NO: 92) | RSDALAR (SEQ ID NO: 41) |
| Intron 1 | 35428 | QSGDLTR (SEQ ID NO: 40) | QRSNLNI (SEQ ID NO: 93) | QSAHRKN (SEQ ID NO: 90) | STAALSY (SEQ ID NO: 91) | DRSALSR (SEQ ID NO: 52) | RSDALAR (SEQ ID NO: 41) |

TABLE 5-continued

Human albumin-specific zinc finger nucleases helix designs

| Target SBS # | F1 | F2 | F3 | F4 | F5 | F6 |
|---|---|---|---|---|---|---|
| Intron 1 34931 | QRTHLTQ (SEQ ID NO: 94) | DRSNLTR (SEQ ID NO: 95) | QSGNLAR (SEQ ID NO: 5) | QKVNRAG (SEQ ID NO: 96) | N/A | N/A |
| Intron 1 33940 | RSDNLSV (SEQ ID NO: 26) | QNANRIT (SEQ ID NO: 97) | DQSNLRA (SEQ ID NO: 73) | QSAHRIT (SEQ ID NO: 98) | TSGNLTR (SEQ ID NO: 11) | HRSARKR (SEQ ID NO: 86) |

TABLE 6

Target sites of Human albumin-specific ZFNs

| Target | SBS # | Target site |
|---|---|---|
| Intron 1 (locus 2) | 35393 | ccTATCCATTGCACTATGCTtttatttaa (SEQ ID NO: 99) |
| Intron 1 (locus 2) | 35394 | ccTATCCATTGCACTATGCTtttatttaa (SEQ ID NO: 99) |
| Intron 1 (locus 2) | 35396 | ccTATCCATTGCACTATGCTtttatttaa (SEQ ID NO: 99) |
| Intron 1 (locus 2) | 35398 | ccTATCCATTGCACTATGCTtttatttaa (SEQ ID NO: 99) |
| Intron 1 (locus 2) | 35399 | ccTATCCATTGCACTATGCTtttatttaa (SEQ ID NO: 99) |
| Intron 1 (locus 2) | 35405 | ccTATCCATTGCACTATGCTtttatttaa (SEQ ID NO: 99) |
| Intron 1 (locus 2) | 35361 | ttTGGGATAGTTATGAAttcaatcttca (SEQ ID NO: 100) |
| Intron 1 (locus 2) | 35364 | ttTGGGATAGTTATGAAttcaatcttca (SEQ ID NO: 100) |
| Intron 1 (locus 2) | 35370 | ttTGGGATAGTTATGAAttcaatcttca (SEQ ID NO: 100) |
| Intron 1 (locus 2) | 35379 | ttTGGGATAGTTATGAAttcaatcttca (SEQ ID NO: 100) |
| Intron 1 (locus 3) | 35458 | ccTGTGCTGTTGATCTCataaatagaac (SEQ ID NO: 101) |
| Intron 1 (locus 3) | 35480 | ccTGTGCTGTTGATctcataaatagaac (SEQ ID NO: 101) |
| Intron 1 (locus 3) | 35426 | ttGTGGTTTTTAAAtAAAGCAtagtgca (SEQ ID NO: 102) |
| Intron 1 (locus 3) | 35428 | ttGTGGTTTTTAAAtAAAGCAtagtgca (SEQ ID NO: 102) |
| Intron 1 (locus 4) | 34931 | acCAAGAAGACAGActaaaatgaaaata (SEQ ID NO: 103) |
| Intron 1 (locus 4) | 33940 | ctGTTGATAGACACTAAAAGagtattag (SEQ ID NO: 104) |

These nucleases were tested in pairs to determine the pair with the highest activity. The resultant matrices of tested pairs are shown in Tables 7 and 8, below where the ZFN used for the right side of the dimer is shown across the top of each matrix, and the ZFN used for the left side of the dimer is listed on the left side of each matrix. The resultant activity, as determined by percent of mismatch detected using the Cel-I assay is shown in the body of both matrices:

TABLE 7

Activity of Human albumin-specific ZFNs (% mutated targets)

| | 35393 | 35394 | 35396 | 35398 | 35399 | 35405 | ave. |
|---|---|---|---|---|---|---|---|
| 35361 | 18 | 19 | 25 | 22 | 23 | 21 | 21 |
| 35364 | n.d. | 24 | 23 | 19 | 21 | 21 | 22 |
| 35370 | 21 | 19 | 22 | n.d. | 22 | 23 | 21 |
| 35379 | 21 | 21 | n.d. | 19 | 19 | 21 | 20 |

(note: 'n.d.' means the assay on this pair was not done)

TABLE 8

Activity of Human albumin-specific ZFNs (% mutated targets))

| | 35458 | 35480 | ave. |
|---|---|---|---|
| 35426 | 4.5 | 7 | 3 |
| 35428 | 4.9 | 6 | 3.6 |

Thus, highly active nucleases have been developed that recognize target sequences in intron 1 of human albumin.

Example 6

Design of Albumin Specific TALENs

TALENs were designed to target sequences within human albumin intron 1. Base recognition was achieved using the canonical RVD-base correspondences (the "TALE code: NI for A, HD for C, NN for G (NK in half repeat), NG for T). TALENs were constructed as previously described (see co-owned U.S. Patent Publication No. 2011/0301073). Targets for a subset of TALENs were conserved in cynomolgus monkey and rhesus macaque albumin genes (for details, see co-owned U.S. Pat. Nos. 9,394,545 and 9,150,847). The TALENs were constructed in the "+17" and "+63" TALEN backbones as described in U.S. Patent Publication No. 2011/0301073. The targets and numeric identifiers for the TALENs tested are shown below in Table 9.

TABLE 9

Albumin specific TALENs

| SBS # | site | # of RVDs | SEQ ID NO: |
|---|---|---|---|
| 102249 | gtTGAAGATTGAATTCAta | 15 | 105 |
| 102250 | gtTGAAGATTGAATTCATAac | 17 | 106 |
| 102251 | gtGCAATGGATAGGTCTtt | 15 | 107 |

TABLE 9-continued

Albumin specific TALENs

| SBS # | site | # of RVDs | SEQ ID NO: |
|---|---|---|---|
| 102252 | atAGTGCAATGGATAGGtc | 15 | 108 |
| 102253 | atTGAATTCATAACTATcc | 15 | 109 |
| 102254 | atTGAATTCATAACTATCCca | 17 | 110 |
| 102255 | atAAAGCATAGTGCAATGGat | 17 | 111 |
| 102256 | atAAAGCATAGTGCAATgg | 15 | 112 |
| 102257 | ctATGCTTTATTTAAAAac | 15 | 113 |
| 102258 | ctATGCTTTATTTAAAAACca | 17 | 114 |
| 102259 | atTTATGAGATCAACAGCAca | 17 | 115 |
| 102260 | ctATTTATGAGATCAACAGca | 17 | 116 |
| 102261 | ttCATTTTAGTCTGTCTTCtt | 17 | 117 |
| 102262 | atTTTAGTCTGTCTTCTtg | 15 | 118 |
| 102263 | ctAATACTCTTTTAGTGTct | 16 | 119 |
| 102264 | atCTAATACTCTTTTAGTGtc | 17 | 120 |
| 102265 | atAATTGAACATCATCCtg | 15 | 121 |
| 102266 | atAATTGAACATCATCCTGag | 17 | 122 |
| 102267 | atATTGGGCTCTGATTCCTac | 17 | 123 |
| 102268 | atATTGGGCTCTGATTCct | 15 | 124 |
| 102269 | ttTTTCTGTAGGAATCAga | 15 | 125 |
| 102270 | ttTTTCTGTAGGAATCAGag | 16 | 126 |
| 102271 | ttATGCATTTGTTTCAAaa | 15 | 127 |
| 102272 | atTATGCATTTGTTTCAaa | 15 | 128 |

The TALENs were then tested in pairs in HepG2 cells for the ability to induce modifications at their endogenous chromosomal targets, and the results showed that many proteins bearing the +17 truncation point were active. Similarly, many TALENs bearing the +63 truncation point were also active (see Table 10). Side by side comparisons with three sets of non-optimized albumin ZFNs (see Table 10) showed that the TALENs and ZFNs have activities that are in the same approximate range.

TABLE 10

TALEN-induced target modification in HepG2-C3a cells

| Sample pair | TALEN C17 | % modification, C17 | TALEN C63 | % modification, C63 | Gap |
|---|---|---|---|---|---|
| 1 | 102251:102249 | 15 | 102251:102249 | 0 | 12 |
| 2 | 102251:102250 | 0 | 102251:102250 | 0 | 10 |
| 3 | 102252:102249 | 0 | 102252:102249 | 8.3 | 15 |
| 4 | 102252:102250 | 32 | 102252:102250 | 8.0 | 13 |
| 5 | 102255:102253 | 38 | 102255:102253 | 21 | 13 |
| 6 | 102255:102254 | 43 | 102255:102254 | 0 | 11 |
| 7 | 102256:102253 | 0 | 102256:102253 | 23 | 15 |
| 8 | 102256:102254 | 28 | 102256:102254 | 16 | 13 |
| 9 | 102259:102257 | 18 | 102259:102257 | 15 | 13 |
| 10 | 102259:102258 | 15 | 102259:102258 | 0 | 11 |
| 11 | 102260:102257 | 15 | 102260:102257 | 13 | 15 |
| 12 | 102260:102258 | 24 | 102260:102258 | 11 | 13 |
| 13 | 102263:102261 | 0 | 102263:102261 | 16 | 17 |
| 14 | 102263:102262 | 0 | 102263:102262 | 15 | 16 |
| 15 | 102264:102261 | 0 | 102264:102261 | 22 | 18 |
| 16 | 102264:102262 | 0 | 102264:102262 | 17 | 17 |
| 20 | 102267:102265 | 47 | 102267:102265 | 9.8 | 13 |
| 21 | 102267:102266 | 4.7 | 102267:102266 | 0 | 11 |
| 22 | 102268:102265 | 4.2 | 102268:102265 | 7.9 | 15 |
| 23 | 102268:102266 | 10 | 102268:102266 | 0 | 13 |
| 24 | 102271:102269 | 14 | 102271:102269 | 0 | 12 |
| 25 | 102271:102270 | 0 | 102271:102270 | 0 | 11 |
| 26 | 102272:102269 | 0 | 102272:102269 | 0 | 13 |
| 27 | 102272:102270 | 0 | 102272:102270 | 0 | 12 |
| ZFNs | | | | | |
| 17 | 35361:35396 | 31 | 35361:35396 | 29 | 6 |
| 18 | 35426:35458 | 10 | 35426:35458 | 7 | 6 |
| 19 | 34931:33940 | 7.3 | 34931:33940 | 7 | 6 |

As noted previously (see co-owned U.S. Patent Publication No. 2011/0301073), the C17 TALENs have greater activity when the gap size between the two TALEN target sites is approximately 11-15 bp, while the C63 TALENs sustain activity at gap sizes up to 18 bp (see Table 10).

Example 7

Detection of LSD Donor Transgenes In Vivo

Donors for four lysosomal storage disease transgenes were constructed for the purpose of integrating into the mouse albumin gene in intron1. The transgenes were α-galactosidase A (GLA), Acid β-glucosidase (GBA), α-L-iduronidase (IDUA) and Iduronate-2-sulfatase (IDS), genes lacking in Fabry's, Gaucher's, Hurler's and Hunter's diseases, respectively. See, e.g., FIG. 8.

The donors were then used in in vivo studies to observe integration of the transgenes. The murine albumin specific ZFNs and the donors were inserted all into AAV2/8 virus as described in Example 4, and then were injected into mice. In these experiments, the virus was formulated for injection in D-PBS+35 mM NaCl, 5% glycerol and frozen prior to injection. The donor- and nuclease-containing viruses were mixed together prior to freezing. At Day 0, the virus preparation was thawed and administered to the mice by tail vein injection where the total injection volume was 200 μL. At the indicated times, the mice were sacrificed and then serum, liver and spleen were harvested for protein and DNA analysis by standard protocols. The dose groups are shown below in Table 11.

TABLE 11

Treatment groups for LSD transgene integration

| Group | Treatment | N/group/time point |
|---|---|---|
| 1 | murine Alb intron 1 + Fabry@ 1:5 ratio; ZFN @ 3.0e11, Donor @ 1.5e12 | 3 |
| 2 | murine Alb intron 1 + Hunters donor@ 1:5 ratio; ZFN @3.0e11, Donor @ 1.5e12 | 3 |
| 3 | murine Alb intron 1 + Hurlers donor@ 1:5 ratio; ZFN @3.0e11, Donor @ 1.5e12 | 3 |
| 4 | murine Alb intron 1 | 3 |

TABLE 11-continued

Treatment groups for LSD transgene integration

| Group | Treatment | N/group/ time point |
|---|---|---|
| 5 | Fabry donor only | 2 |
| 6 | Hunter's donor only | 2 |
| 7 | Hurler's donor only | 2 |

At day 30, liver homogenates were analyzed by Western blot analysis for the presence of the LSD proteins encoded by the donors. Liver homogenates were analyzed by Western blot using standard methodologies, using the following primary antibodies: α-Galactosidase A (Fabry's)-specific rabbit monoclonal antibody was purchased from Sino Biological, Inc.; Human α-L-Iduronidase (Hurler's)-specific mouse monoclonal antibody was purchased from R&D Systems; Human iduronate 2-Sulfatase (Hunter's)-specific mouse monoclonal was purchased from R&D Systems. The results (See FIGS. 5A through 5D) demonstrate expression, especially in the mice that received both the ZFN containing virus and the transgene donor containing virus.

Figure 2:
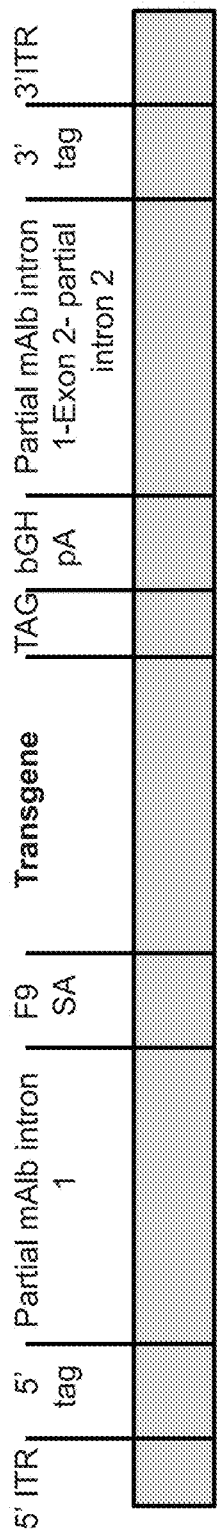
FIG. 2 is a schematic depicting the structure of four AAV donors designed to provide therapeutic transgenes for treatment of Fabry's, Gaucher's, Hurler's and Hunter's diseases. Each donor construct contains the AAV sequences (5'ITR and 3'ITR), flanking homology arms for insertion of the donors into the albumin locus by homology dependent mechanisms, a splice acceptor site, the DNA encoding the replacement enzyme, and a MYC-Flag Tag to allow identification of the integrated donors.
Figure 6:
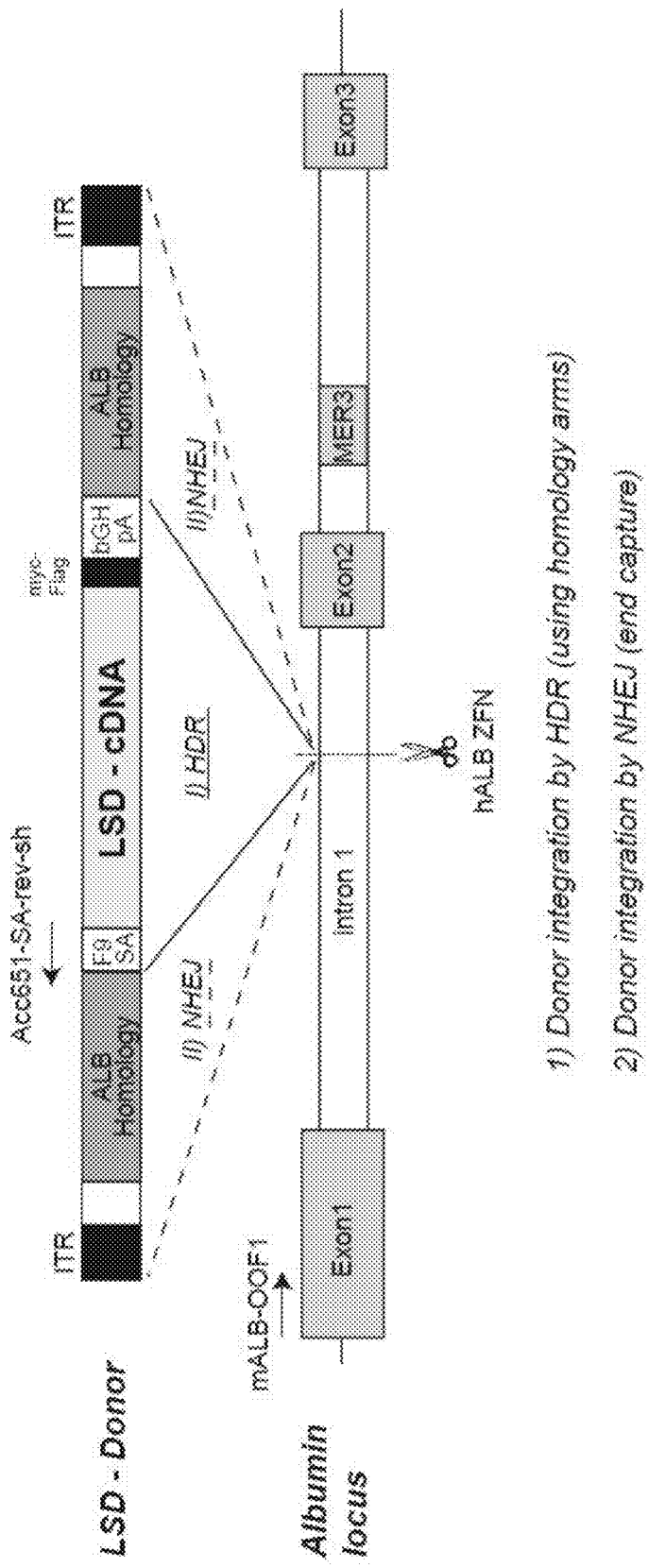
FIG. 6 is a schematic displaying the two types of donor insertion that may occur following ZFN mediated cleavage. NHEJ mediated donor insertion will result in the entire LSD-Donor construct being integrated, whereas HDR-mediated insertion will cause only the cDNA including the F9 splice-acceptor site to be incorporated.
Figures 7A, 7B, 7C:
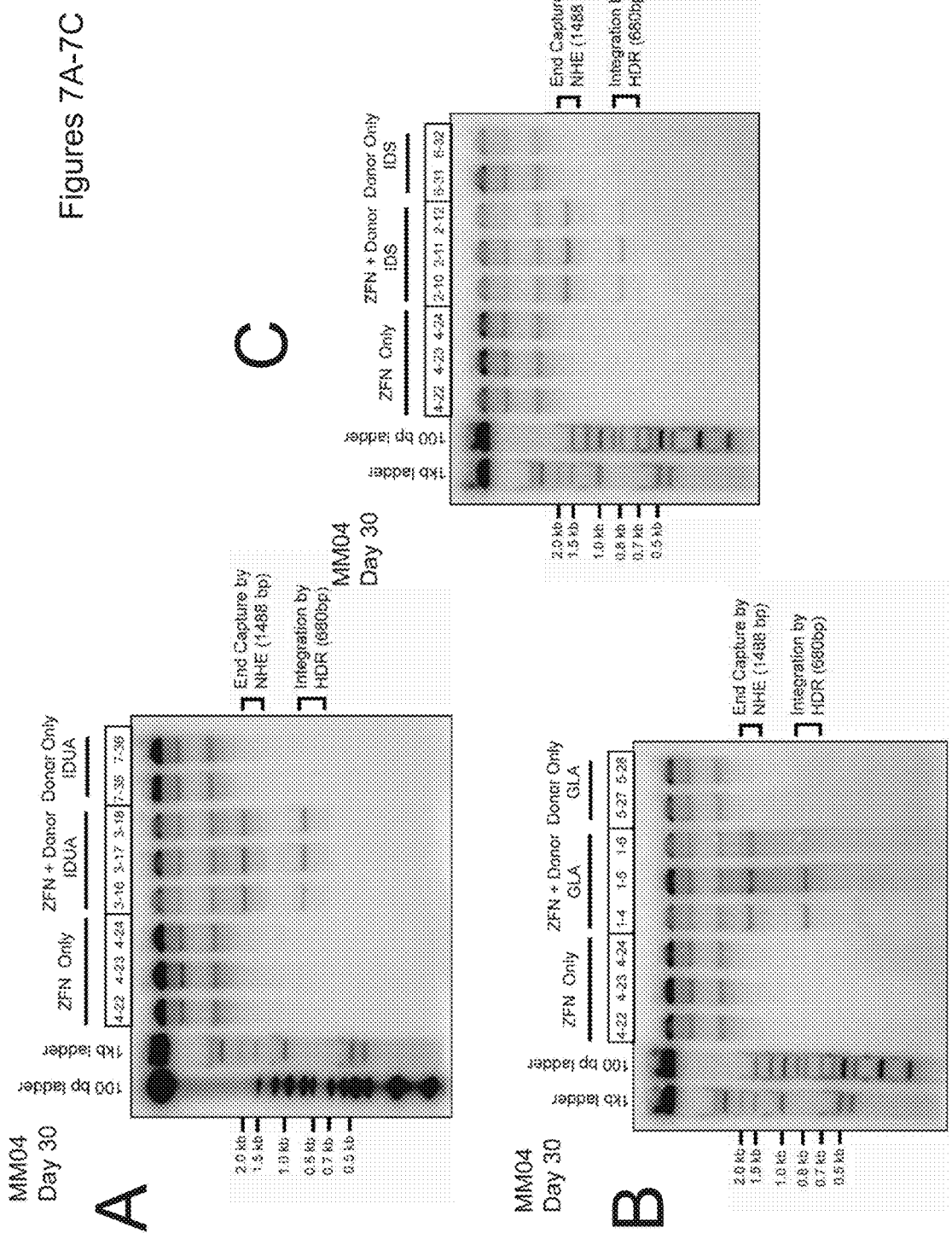
FIGS. 7A through 7C depict the results of $^{32}$P radiolabeled PCR performed on liver homogenates on mice containing the integrated LSD transgenes 30 days after treatment.

The manner of integration of the donor DNA into the albumin locus was also investigated. Following the cleavage at the albumin locus, the donor transgene could be potentially be integrated via homology directed recombination (HDR), utilizing the regions of homology flanking the transgene donor (FIG. 2), or the transgene may be captured during the error-prone non-homologous end joining process (NHEJ). The results of these two alternatives will yield insertions of differing sizes when subject to PCR, using either the Acc651-SA-rev-sh primer (5'AAG AAT AAT TCT TTA GTG GTA 3', SEQ ID NO:129) which binds to the F9 splice acceptor site in all LSD donor constructs and the mALB-OOF1 primer (5' ATGAAGTGGGTAACCTTTCTC 3', SEQ ID NO:130) which binds to the mouse albumin exon 1 upstream of the ZFN cleavage site (see FIG. 6), where the integration of the transgene by HDR will result in insertion of approximately 680 bp while integration via NHEJ will result in integration of approximately 1488 bp. Thus, genomic DNA isolated from the treated mice liver homogenates was subject to PCR in the presence of $^{32}$P-radiolabeled nucleotides and run on a gel. In all three of the transgene integrations, integration via both mechanisms was observed (see FIGS. 7A through 7C).

Figure 8:
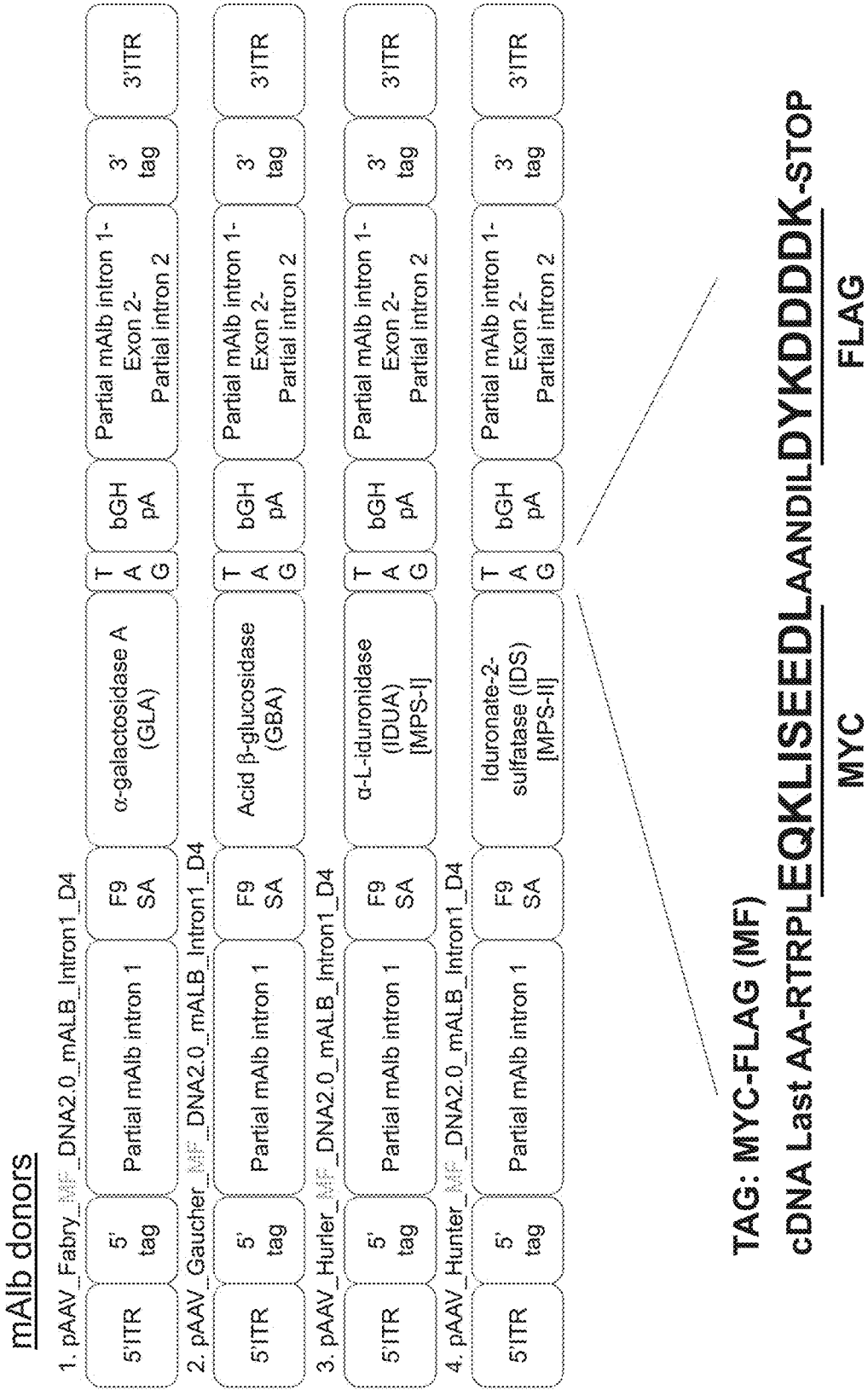
FIG. 8 is a schematic illustrating the design of the LSD donors containing epitope tags. The location and sequences of the Myc and Flag tags are indicated (SEQ ID NO: 134).
Figure 9A:
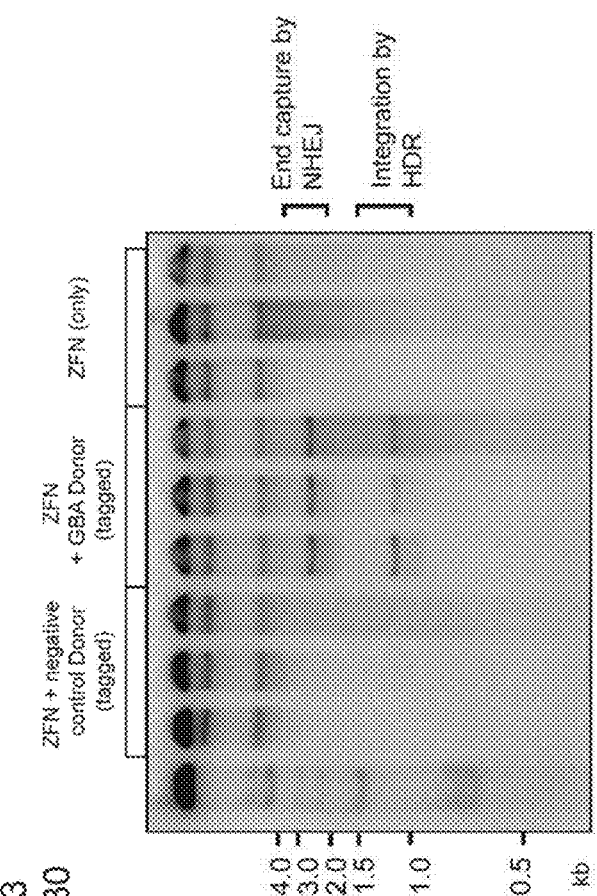
FIGS. 9A and 9B depicts a gel of $^{32}$P radiolabeled PCR done as described above on liver homogenates from mice with integrated LSD donors containing the epitope tags.
Figure 9B:
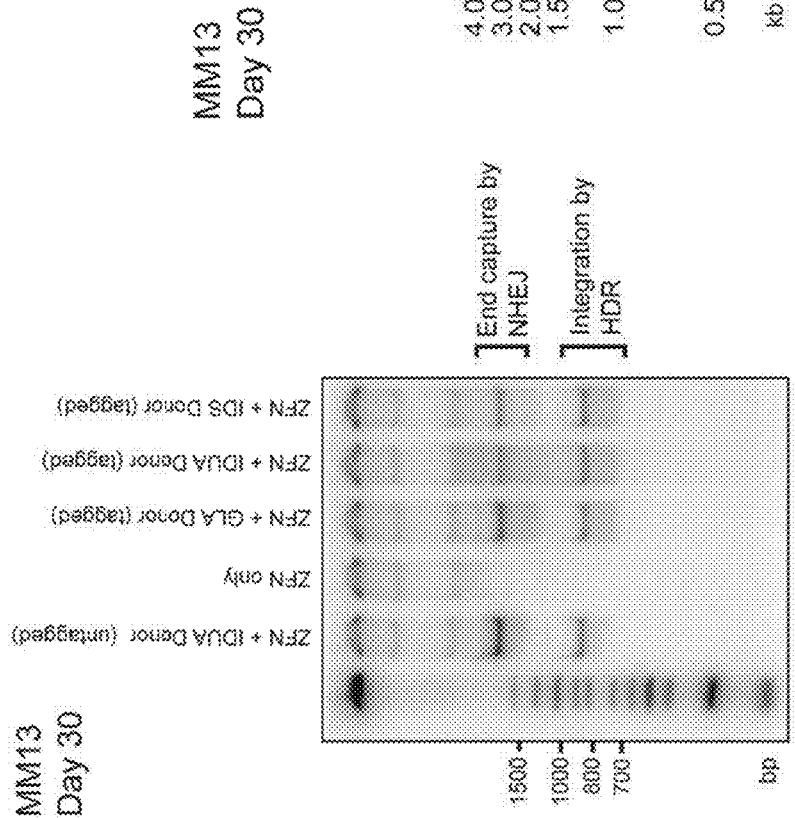

Donor DNAs were also designed to include a tag sequence for later recognition of the protein using the tag specific antibodies. The tag was designed to incorporate two different sequences encoding the Myc (EQKLISEEDL, SEQ ID NO:131) and the Flag (DYKDDDD SEQ ID NO:132) tags. Schematics of the donor designs are shown in FIG. 8. The donors were integrated as described above, and all were capable of integration as demonstrated by PCR (see FIGS. 9A and 9B).

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method for expressing and secreting exogenous glucocerbrosidase (GBA), α-galactosidase A (GLA), iduronate sulftase (IDS), iduronidase (IDUA) protein, or α-glucosidase (GAA) in a liver cell in a human with a deficient GLA, GBA, IDS, IDUA, or GAA gene, the method comprising:
   (i) intravenously injecting one or more adeno-associated viral (AAV) vectors encoding a pair of zinc finger nucleases (ZFNs) into the human, wherein the ZFNs target and cleave intron 1 of an endogenous albumin gene in the liver cell; and
   (ii) intravenously injecting an AAV vector comprising a donor sequence comprising a transgene encoding:
      (a) an exogenous GBA protein into the human with the deficient GBA gene;
      (b) an exogenous GLA protein into the human with the deficient GLA gene;
      (c) an exogenous IDS protein into the human with the deficient IDS gene;
      (d) an exogenous IDUA protein into the human with the deficient IDUA gene, or
      (e) an exogenous GAA protein into the human with the deficient GAA gene, and
   wherein the transgene is flanked by sequences having homology with the endogenous albumin gene,
   such that the transgene is integrated into the endogenous albumin gene in the liver cell, and the liver cell expresses and secretes the exogenous GBA, GLA, IDS, IDUA, or GAA protein.

2. The method of claim 1, wherein the liver cell expresses and secretes the exogenous IDS or IDUA protein.

3. The method of claim 1, wherein expression of the transgene is driven by an endogenous albumin promoter.

4. The method of claim 1, wherein the one or more AAV vectors of step (i) and the AAV vector of step (ii) are co-administered.

5. The method of claim 1, wherein expression of the transgene is driven by an exogenous promoter.

6. The method of claim 1, wherein protein is secreted from the liver into the blood, spleen, kidney, lymph nodes and/or brain of the human subject.

7. A method of treating a human with Gaucher's, Fabry's, Hunter's or Hurler's disease, the method comprising:
   expressing and secreting exogenous OBA protein in a liver cell in the mouse or human with Gaucher's disease,
   expressing and secreting exogenous GLA protein in a liver cell in the mouse or human with Fabry's disease,
   expressing and secreting exogenous IDS protein in a liver cell in the mouse or human with Hunter's/MPS II disease, or
   expressing and secreting exogenous IDUA protein in a liver cell in the mouse or human with Hurler's/MPS I disease
   according to the method of claim 1 such that therapeutic levels of the protein are obtained in the serum of the human.

* * * * *

SEQUENCE LISTING

```
<160> NUMBER OF SEQ ID NOS: 134

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Ser Gly Ser Leu Thr Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ser Asp Ala Leu Ser Thr
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 3

Gln Ser Ala Thr Arg Thr Lys
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Ser Gly His Leu Ser Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Ser Gly Asn Leu Ala Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ser Asp His Leu Ser Ala
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Lys Ser Asn Arg Thr Lys
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Arg Ser Asn Leu Ser Arg
1               5
```

```
<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Trp Arg Ser Ser Leu Arg Ala
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Ser Ser Asp Arg Lys Lys
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Ser Gly Asn Leu Thr Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Arg Ser Thr Arg Arg Gln
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Arg Gly Thr Leu Ala Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 14

Thr Ser Ala Asn Leu Ser Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Arg Ser Ala Leu Ala Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ser Asp His Leu Ser Glu
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

His Arg Ser Asp Arg Thr Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ser Gly Ala Leu Ala Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ser Gly His Leu Ser Arg
1               5
```

```
<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Ser Asp Asn Leu Ser Thr
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Gly Arg Asn Leu Arg His
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ser Asp Asn Leu Ala Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Ser Asn Ala Leu Asn Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Lys Gln Val Leu Val Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 25

Gln Ser Thr Pro Leu Phe Ala
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ser Asp Asn Leu Ser Val
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

His Ser Asn Ala Arg Lys Thr
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Ser Asp Ser Leu Ser Ala
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ser Asp Ser Leu Ser Val
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ser Asp Asn Leu Ser Glu
1               5
```

```
<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Glu Arg Ala Asn Arg Asn Ser
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Ser Ala Asn Arg Thr Lys
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ser Asp Ala Leu Thr Gln
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Ser Gly His Leu Ala Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Ser Asp His Leu Thr Gln
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 36

Arg Ser Asp His Leu Ser Gln
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Trp Arg Ser Ser Leu Val Ala
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Ser Asp Val Leu Ser Glu
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Asn Gln His Arg Lys Thr
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Ser Gly Asp Leu Thr Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ser Asp Ala Leu Ala Arg
1               5
```

```
<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Arg Asp Pro Leu Ile Asn
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ile Arg Ser Thr Leu Arg Asp
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Tyr Ser Ser Thr Arg Asn Ser
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Tyr Trp Ser Arg Thr Val
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ser Ser Asp Leu Ser Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 47

Arg Thr Asp Ala Leu Arg Gly
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Lys Ser Pro Leu Asn Thr
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Ala Glu Asn Leu Lys Ser
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Arg Ala His Leu Asn Gln
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Asp Thr Asn Arg Phe Lys
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Arg Ser Ala Leu Ser Arg
1               5
```

-continued

```
<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Ser Ser Asn Arg Lys Thr
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Ser Asp His Leu Ser Arg
1               5

<210> SEQ ID NO 55
<211> LENGTH: 28
<212> TYPE: DNA
<213> ORGANISM: Mus sp.

<400> SEQUENCE: 55
ctgaaggtgg caatggttcc tctctgct                                            28

<210> SEQ ID NO 56
<211> LENGTH: 28
<212> TYPE: DNA
<213> ORGANISM: Mus sp.

<400> SEQUENCE: 56
tttcctgtaa cgatcgggaa ctggcatc                                            28

<210> SEQ ID NO 57
<211> LENGTH: 28
<212> TYPE: DNA
<213> ORGANISM: Mus sp.

<400> SEQUENCE: 57
aagatgccag ttcccgatcg ttacagga                                            28

<210> SEQ ID NO 58
<211> LENGTH: 28
<212> TYPE: DNA
<213> ORGANISM: Mus sp.

<400> SEQUENCE: 58
agggagtagc ttaggtcagt gaagagaa                                            28

<210> SEQ ID NO 59
<211> LENGTH: 28
<212> TYPE: DNA
<213> ORGANISM: Mus sp.

<400> SEQUENCE: 59
acgtagagaa caacatctag attggtgg                                            28
```

```
<210> SEQ ID NO 60
<211> LENGTH: 28
<212> TYPE: DNA
<213> ORGANISM: Mus sp.

<400> SEQUENCE: 60
ctgtaataga aactgactta cgtagctt                                    28

<210> SEQ ID NO 61
<211> LENGTH: 28
<212> TYPE: DNA
<213> ORGANISM: Mus sp.

<400> SEQUENCE: 61
agggaatgtg aaatgattca gatatata                                    28

<210> SEQ ID NO 62
<211> LENGTH: 28
<212> TYPE: DNA
<213> ORGANISM: Mus sp.

<400> SEQUENCE: 62
ccatggccta acaacagttt atcttctt                                    28

<210> SEQ ID NO 63
<211> LENGTH: 28
<212> TYPE: DNA
<213> ORGANISM: Mus sp.

<400> SEQUENCE: 63
cttggctgtg taggagggga gtagcagt                                    28

<210> SEQ ID NO 64
<211> LENGTH: 28
<212> TYPE: DNA
<213> ORGANISM: Mus sp.

<400> SEQUENCE: 64
ttcctaagtt ggcagtggca tgcttaat                                    28

<210> SEQ ID NO 65
<211> LENGTH: 28
<212> TYPE: DNA
<213> ORGANISM: Mus sp.

<400> SEQUENCE: 65
ctttggcttt gaggattaag catgccac                                    28

<210> SEQ ID NO 66
<211> LENGTH: 28
<212> TYPE: DNA
<213> ORGANISM: Mus sp.

<400> SEQUENCE: 66
acttggctcc aagatttata gccttaaa                                    28

<210> SEQ ID NO 67
<211> LENGTH: 28
<212> TYPE: DNA
<213> ORGANISM: Mus sp.

<400> SEQUENCE: 67
caggaaagta agataggaag gaatgtga                                    28
```

-continued

```
<210> SEQ ID NO 68
<211> LENGTH: 28
<212> TYPE: DNA
<213> ORGANISM: Mus sp.

<400> SEQUENCE: 68
ctggggtaaa tgtctccttg ctcttctt                                          28

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gttgccagcc atctgttgtt t                                                 21

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gacagtggga gtggcacctt                                                   20

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 71
ctcccccgtg ccttccttga cc                                                22

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Arg His Asn Leu Arg Ala
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asp Gln Ser Asn Leu Arg Ala
1               5
```

```
<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Pro Tyr Thr Leu Arg Leu
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

His Arg Ser Asn Leu Asn Lys
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Leu Lys Trp Asn Leu Arg Thr
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Trp Lys Trp Asn Leu Arg Ala
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Leu Met Gln Asn Arg Asn Gln
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 79

Leu Lys Gln His Leu Asn Glu
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Arg Arg Tyr Tyr Leu Arg Leu
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

His Leu Gly Asn Leu Lys Thr
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Arg Asp Trp Arg Arg Asp
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gln Arg Ser Asn Leu Val Arg
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Leu Lys His His Leu Thr Asp
1               5
```

```
<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asp Lys Ser Tyr Leu Arg Pro
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

His Arg Ser Ala Arg Lys Arg
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Trp Arg Ser Ser Leu Lys Thr
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asn Arg His His Leu Lys Ser
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Ser Gly Asn Leu His Val
1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 90

Gln Ser Ala His Arg Lys Asn
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ser Thr Ala Ala Leu Ser Tyr
1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Thr Ser Gly Ser Leu Ser Arg
1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Arg Ser Asn Leu Asn Ile
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Arg Thr His Leu Thr Gln
1               5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Asp Arg Ser Asn Leu Thr Arg
1               5
```

```
<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Lys Val Asn Arg Ala Gly
1               5

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Asn Ala Asn Arg Ile Thr
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Ser Ala His Arg Ile Thr
1               5

<210> SEQ ID NO 99
<211> LENGTH: 28
<212> TYPE: DNA
<213> ORGANISM: Homo sapiens

<400> SEQUENCE: 99
cctatccatt gcactatgct ttatttaa                                        28

<210> SEQ ID NO 100
<211> LENGTH: 28
<212> TYPE: DNA
<213> ORGANISM: Homo sapiens

<400> SEQUENCE: 100
tttgggatag ttatgaattc aatcttca                                        28

<210> SEQ ID NO 101
<211> LENGTH: 28
<212> TYPE: DNA
<213> ORGANISM: Homo sapiens

<400> SEQUENCE: 101
cctgtgctgt tgatctcata aatagaac                                        28

<210> SEQ ID NO 102
<211> LENGTH: 28
<212> TYPE: DNA
<213> ORGANISM: Homo sapiens
```

<400> SEQUENCE: 102
ttgtggtttt taaataaagc atagtgca                28

<210> SEQ ID NO 103
<211> LENGTH: 28
<212> TYPE: DNA
<213> ORGANISM: Homo sapiens

<400> SEQUENCE: 103
accaagaaga cagactaaaa tgaaaata                28

<210> SEQ ID NO 104
<211> LENGTH: 28
<212> TYPE: DNA
<213> ORGANISM: Homo sapiens

<400> SEQUENCE: 104
ctgttgatag acactaaaag agtattag                28

<210> SEQ ID NO 105
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gttgaagatt gaattcata                19

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gttgaagatt gaattcataa c                21

<210> SEQ ID NO 107
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gtgcaatgga taggtcttt                19

<210> SEQ ID NO 108
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
atagtgcaat ggataggtc                19

<210> SEQ ID NO 109
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
attgaattca taactatcc                                                    19

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
attgaattca taactatccc a                                                 21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
ataaagcata gtgcaatgga t                                                 21

<210> SEQ ID NO 112
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
ataaagcata gtgcaatgg                                                    19

<210> SEQ ID NO 113
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ctatgcttta tttaaaaac                                                    19

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ctatgcttta tttaaaaacc a                                                 21

```
<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
atttatgaga tcaacagcac a                                              21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ctatttatga gatcaacagc a                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
ttcattttag tctgtcttct t                                              21

<210> SEQ ID NO 118
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
attttagtct gtcttcttg                                                 19

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ctaatactct tttagtgtct                                                20

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
atctaatact cttttagtgt c                                              21
```

```
<210> SEQ ID NO 121
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
ataattgaac atcatcctg                                                 19

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ataattgaac atcatcctga g                                              21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
atattgggct ctgattccta c                                              21

<210> SEQ ID NO 124
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
atattgggct ctgattcct                                                 19

<210> SEQ ID NO 125
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
tttttctgta ggaatcaga                                                 19

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
tttttctgta ggaatcagag                                                20
```

```
<210> SEQ ID NO 127
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ttatgcattt gtttcaaaa                                                  19

<210> SEQ ID NO 128
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
attatgcatt tgtttcaaa                                                  19

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
aagaataatt ctttagtggt a                                               21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
atgaagtggg taacctttct c                                               21

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Glu Gln Lys Leu Ile Ser Glu Glu Asp Leu
1               5                   10

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asp Tyr Lys Asp Asp Asp Asp
1               5
```

```
<210> SEQ ID NO 133
<211> LENGTH: 9
<212> TYPE: PRT
<213> ORGANISM: Unknown
<220> FEATURE:
<223> OTHER INFORMATION: Description of Unknown: Unknown LAGLIDADG
      family sequence

<400> SEQUENCE: 133

Leu Ala Gly Leu Ile Asp Ala Asp Gly
1               5

<210> SEQ ID NO 134
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Arg Thr Arg Pro Leu Glu Gln Lys Leu Ile Ser Glu Glu Asp Leu Ala
1               5                   10                  15

Ala Asn Asp Ile Leu Asp Tyr Lys Asp Asp Asp Lys
            20                  25
```